United States Patent
Saito

(10) Patent No.: US 10,902,589 B2
(45) Date of Patent: Jan. 26, 2021

(54) MEDICAL IMAGE DIAGNOSIS APPARATUS AND MEDICAL IMAGE PROCESSING APPARATUS

(71) Applicant: Canon Medical Systems Corporation, Otawara (JP)

(72) Inventor: Kazuyo Saito, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 225 days.

(21) Appl. No.: 16/143,832

(22) Filed: Sep. 27, 2018

(65) Prior Publication Data

US 2019/0096061 A1    Mar. 28, 2019

(30) Foreign Application Priority Data

Sep. 28, 2017  (JP) .................................. 2017-187379

(51) Int. Cl.

| G06K 9/00 | (2006.01) |
|---|---|
| G06T 7/00 | (2017.01) |
| A61B 6/03 | (2006.01) |
| G16H 30/40 | (2018.01) |
| A61B 6/00 | (2006.01) |
| G06T 7/11 | (2017.01) |

(Continued)

(52) U.S. Cl.
CPC ............ G06T 7/0012 (2013.01); A61B 6/032 (2013.01); A61B 6/463 (2013.01); A61B 6/481 (2013.01); A61B 6/486 (2013.01); A61B 6/5205 (2013.01); G06T 7/11 (2017.01); G06T 11/206 (2013.01); G16H 30/20 (2018.01);

*G16H 30/40* (2018.01); *A61B 5/0073* (2013.01); *A61B 5/055* (2013.01); *A61B 6/4035* (2013.01); *A61B 6/507* (2013.01)

(58) Field of Classification Search
CPC ....... A61B 5/0073; A61B 5/055; A61B 6/032; A61B 6/4035; A61B 6/463; A61B 6/481; A61B 6/486; A61B 6/507; A61B 6/5205; G06T 11/206; G06T 7/0012; G06T 7/11; G16H 30/20; G16H 30/40
See application file for complete search history.

(56) References Cited

U.S. PATENT DOCUMENTS

| 2011/0263973 A1* | 10/2011 | Bernhardt | ............. | A61B 6/486 |
| | | | | 600/431 |
| 2013/0012814 A1* | 1/2013 | Taguchi | ................ | A61B 6/469 |
| | | | | 600/431 |

(Continued)

FOREIGN PATENT DOCUMENTS

| JP | 2009-207755 | 9/2009 |
| JP | 2016-097241 | 5/2016 |

*Primary Examiner* — Tom Y Lu
(74) *Attorney, Agent, or Firm* — Oblon, McClelland, Maier & Neustadt, L.L.P.

(57) ABSTRACT

According to one embodiment, a medical image diagnosis apparatus includes an image acquisition unit, a data acquisition unit, a generation unit, and a display control unit. The image acquisition unit acquires medical image data of a plurality of time phases. The data acquisition unit acquires pixel value data of the time phases with respect to each of specified regions based on the medical image data. The generation unit generates display information based on the pixel value data of the time phases. The display control unit displays the display information in association with the regions in medical image data of an arbitrary time phase.

12 Claims, 18 Drawing Sheets

(51) Int. Cl.
*G16H 30/20* (2018.01)
*G06T 11/20* (2006.01)
*A61B 5/055* (2006.01)
*A61B 5/00* (2006.01)

(56) References Cited

U.S. PATENT DOCUMENTS

| | | | |
|---|---|---|---|
| 2013/0079626 A1* | 3/2013 | Shmatukha | A61B 6/5205 600/420 |
| 2016/0078619 A1* | 3/2016 | Hsieh | A61B 6/06 378/4 |

* cited by examiner

MEDICAL IMAGE DIAGNOSIS APPARATUS AND MEDICAL IMAGE PROCESSING APPARATUS

CROSS-REFERENCE TO RELATED APPLICATION

This application is based upon and claims the benefit of priority from Japanese Patent Application No. 2017-187379, filed on 2017 Sep. 28; the entire contents of which are incorporated herein by reference.

FIELD

Embodiments described herein relate generally to a medical image diagnosis apparatus and a medical image processing apparatus.

BACKGROUND

In recent years, a subject is sometimes examined with a medical image diagnosis apparatus that collects information on the inside of the subject and generates a medical image by imaging the inside of the subject based on the information. Examples of the medical image diagnosis apparatus include X-ray computed tomography (CT) systems, magnetic resonance imaging (MRI) equipment, and the like.

CT images (medical images) captured by the X-ray CT system are not only images of a single moment, but also include those photographed continuously or intermittently over time. This enables the observation of changes in images as time elapses. Therefore, the CT image can serve as a functional image as well as a morphological image. Besides, because of the image resolution and the examination speed, the X-ray CT system is widely used from the initial examination of the subject to the check of his/her medical condition during and after treatment.

The subject generally undergoes a plurality of examinations utilizing the X-ray CT system in the treatment of one disease, although it depends on the type and condition of the disease. Further, the subject may be photographed a plurality of times for non-contrast scan, contrast scan (arterial phase, venous phase, equilibrium phase, etc.), and the like in one examination. As a result, many medical images are captured by the photographing. Thus, a plurality of medical images can be compared with respect to the same site to be diagnosed.

The medical images can illustrate various states of the site to be diagnosed. However, for example, as the number of medical images captured in one examination increases, it becomes difficult to search and display medical images suitable for diagnosis or the like.

In addition, for example, when changes in the site to be diagnosed are checked by using a plurality of medical images, conditions suitable for comparison are set to display the medical images basically based on the skill and sense of the operator. Therefore, the medical images to be displayed may vary depending on the operator.

DETAILED DESCRIPTION

In general, according to one embodiment, a medical image diagnosis apparatus includes an image acquisition unit, a data acquisition unit, a generation unit, and a display control unit. The image acquisition unit acquires medical image data of a plurality of time phases. The data acquisition unit acquires pixel value data of the time phases with respect to each of specified regions based on the medical image data. The generation unit generates display information based on the pixel value data of the time phases. The display control unit displays the display information in association with the regions in medical image data of an arbitrary time phase.

Exemplary embodiments will be described in detail with reference to the drawings.

First Embodiment

[Configuration of Medical Image Diagnosis Apparatus]

Figure 1:
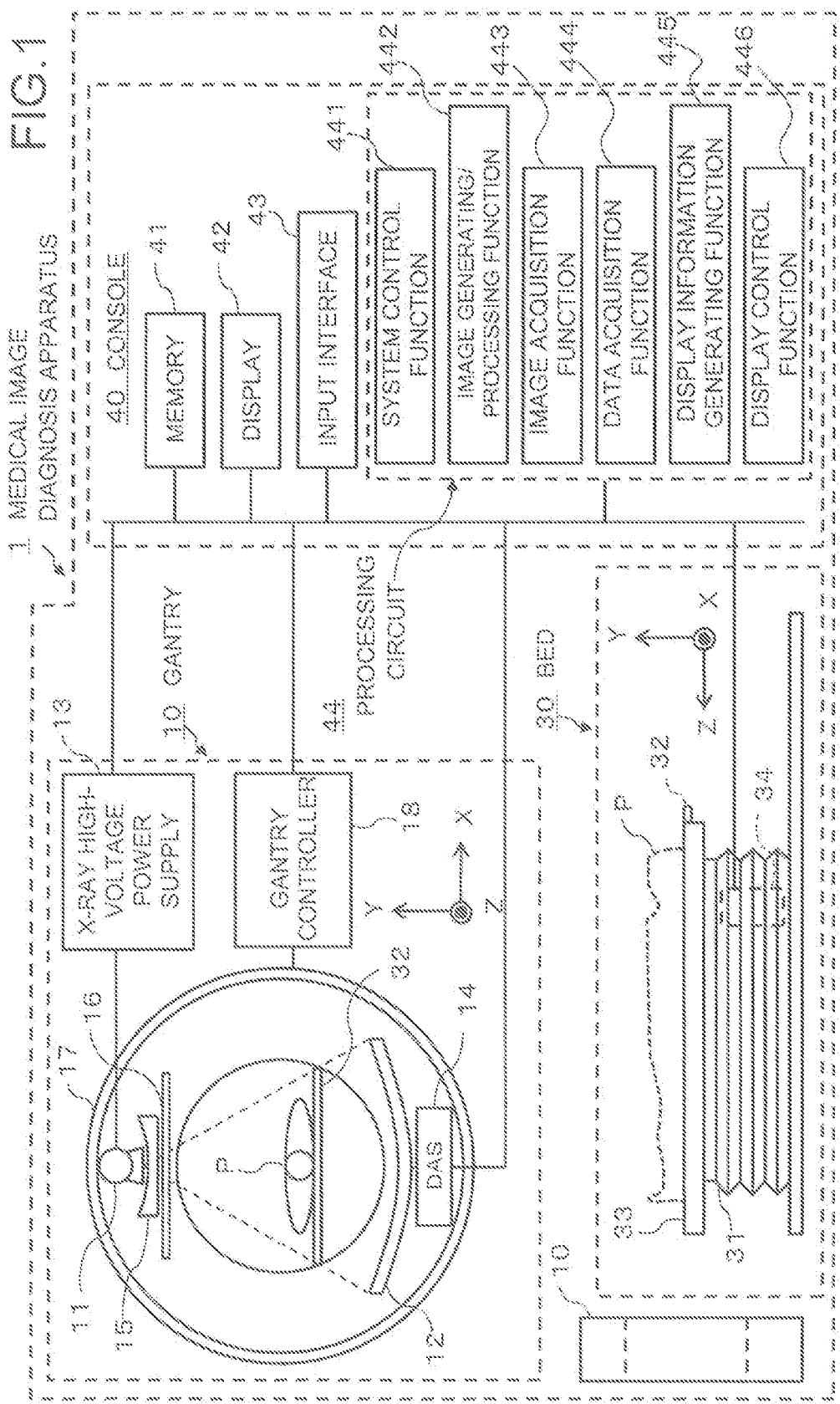
FIG. 1 is a block diagram illustrating the overall configuration of a medical image diagnosis apparatus according to a first embodiment.

FIG. 1 is a block diagram illustrating the overall configuration of a medical image diagnosis apparatus 1 according to a first embodiment. In the following description of the first embodiment, an X-ray CT system is described as an example of the medical image diagnosis apparatus. However, the medical image diagnosis apparatus may be another apparatus than the X-ray CT system, such as MRI equipment described above.

The medical image diagnosis apparatus (X-ray CT system) 1 includes a gantry 10, a bed 30, and a console 40. The gantry 10 is a device configured to acquire information on the inside of a subject P to be examined or treated to generate a medical image of the subject P. The bed 30 is a device on which the subject P is placed. The console 40 is configured to control the entire medical image diagnosis apparatus 1 including the gantry 10 and the bed 30.

The gantry 10 includes an X-ray generator 11, an X-ray detector 12, an X-ray high-voltage power supply 13, a data acquisition system (DAS) 14, a wedge 15, a collimator 16, a rotating frame 17, and a controller 18.

The X-ray generator 11 includes an X-ray tube (vacuum tube) that, for example, in response to the supply of high voltage from the X-ray high-voltage power supply 13 (described later), irradiates thermoelectrons from a cathode (sometimes referred to as "filament") to an anode (sometimes referred to as "target").

The X-ray detector 12 detects X-rays irradiated from the X-ray generator 11 and having passed through the subject P. The X-ray detector 12 outputs an electric signal corresponding to the dose of the X-rays to the DAS 14 (described later). The X-ray detector 12 includes, for example, a plurality of X-ray detection element arrays in which a plurality of X-ray detection elements are arranged in the channel direction along one circular arc around the focus of the X-ray tube. The X-ray detector 12 has a structure in which, for example, the X-ray detection element arrays, where the X-ray detection elements are arranged in the channel direction, are arrayed in the slice direction.

The X-ray detector 12 may be, for example, an indirect-conversion detector that includes a grid, a scintillator array, and an optical sensor array.

The scintillator array has a plurality of scintillators. The scintillators are formed of scintillation crystals that emit light with an amount of photons corresponding to the incident X-ray dose.

The grid is arranged on a surface of the scintillator array on the side where X-rays are incident, and includes an X-ray shielding plate having the function of absorbing scattered X-rays.

The optical sensor array has the function of converting X-rays into electric signals corresponding to the amount of light from the scintillator array. The optical sensor array includes, for example, an optical sensor such as a photomultiplier tube (PMT).

The X-ray detector 12 may be a direct-conversion detector having a semiconductor element that converts incident X-rays into electric signals.

The X-ray high-voltage power supply 13 is provided with electric circuits such as a transformer and a rectifier. The X-ray high-voltage power supply 13 includes a high-voltage generator having the function of generating a high voltage to be applied to the X-ray generator 11, and an X-ray controller that controls the output voltage according to X-rays irradiated by the X-ray generator 11. The high-voltage generator may be of transformer type or inverter type.

The X-ray high-voltage power supply 13 may be arranged on the rotating frame 17 (described later) or on the side of a fixed frame (not illustrated) of the gantry 10. The fixed frame rotatably supports the rotating frame 17.

The DAS 14 includes at least an amplifier and an A/D converter. The amplifier amplifies an electric signal output from each of the X-ray detection elements of the X-ray detector 12. The A/D converter converts the electric signal into a digital signal. The DAS 14 generates detection data (pure raw data). The detection data generated by the DAS 14 is sent to the console 40.

The wedge 15 is a filter for adjusting the dose of X-rays irradiated from the X-ray generator 11. Specifically, the wedge 15 is a filter that attenuates X-rays irradiated from the X-ray generator 11 as the X-rays pass therethrough such that the subject P is irradiated with the X-rays of a predetermined distribution. The wedge 15 is made of, for example, aluminum processed so as to have a predetermined target angle or a predetermined thickness. The wedge 15 is also called "wedge filter" or "bow-tie filter".

The collimator 16 includes lead plates or the like for narrowing the irradiation range of the X-rays having passed through the wedge 15. The collimator 16 forms a slit by a combination of a plurality of lead plates or the like.

The rotating frame 17 supports the X-ray generator 11 and the X-ray detector 12 arranged therein at positions facing each other. The rotating frame 17 is an annular frame that rotates the X-ray generator 11 and the X-ray detector 12 according to a signal from the controller 18 (described later). In addition to the X-ray generator 11 and the X-ray detector 12, the rotating frame 17 also supports the X-ray high-voltage power supply 13 and the DAS 14 arranged therein.

With this structure, the rotating frame 17 performs imaging while the X-ray generator 11 and the X-ray detector 12 are rotating integrally around the subject P in the center of rotation. The rotating frame 17 irradiates the subject P with X-rays and detects the X-rays that have passed through the subject P. The rotating frame 17 is provided with an annular opening to let the subject P (top plate 32) enter and exit.

The rotating frame 17 is provided with a transmitter having a light emitting diode (LED) to transmit detection data generated by the DAS 14 to a receiver via optical communication. The receiver has a photodiode provided in a non-rotating part of the gantry 10 such as, for example, the fixed frame (not illustrated). The detection data received by the receiver is sent to the console 40.

The detection data need not necessarily transmitted via optical communication from the rotating frame 17 to the non-rotating part of the gantry 10, and any method can be employed as long as it implements non-contact data transmission.

As illustrated in FIG. 1, the rotation axis of the rotating frame 17 being not tilted or the direction parallel to the longitudinal direction of the top plate 32 of the bed 30 (described later) is defined as Z-axis direction. An axial direction perpendicular to the Z-axis direction and horizontal to the floor surface is defined as X-axis direction. An axial direction perpendicular to the Z-axis direction and vertical to the floor surface is defined as Y-axis direction.

The controller 18 includes a processing circuit having a central processing unit (CPU) and the like, and driving mechanisms such as a motor and an actuator. The controller 18 has the function of controlling the operation of the gantry 10 and the bed 30 in response to an input signal from an input interface attached to the console 40 or the gantry 10. Upon receipt of an input signal, for example, the controller 18 controls the rotating frame 17 to rotate, controls the gantry 10 to tilt, or controls the bed 30 and the top plate 32 to move.

The controller 18 may be located in the gantry 10 or may be located in the console 40.

The controller 18 tilts the gantry 10 by rotating the rotating frame 17 about an axis parallel to the X-axis direction based on tilt angle information provided through the input interface attached to the gantry 10, The bed 30 is a device on which the subject P to be scanned is placed, and moves the subject P. The bed 30 includes a base 31, the top plate 32, a support frame 33, and a bed driving device 34.

The base 31 is a housing that supports the support frame 33 (the top plate 32) movably in the vertical direction (the Y direction indicated by the arrow in the frame of the bed 30 in FIG. 1). The top plate 32 is a plate on which the subject P is placed. The support frame 33 supports the top plate 32 on its upper surface.

The bed driving device 34 is a motor or actuator to move the top plate 32 on which the subject P is placed in the longitudinal direction (Z direction) of the top plate 32 or in the Y direction (vertical direction with respect to the floor surface). The bed driving device 34 is driven in response to an input signal from the console 40, and moves the top plate 32 in the directions described above.

In addition to the top plate 32, the bed driving device 34 may also move the support frame 33 in the longitudinal direction of the top plate 32. Since the bed driving device 34 is located in the base 31, it is illustrated by a broken line in FIG. 1.

The console 40 includes a memory 41, a display 42, an input interface 43, and a processing circuit 44.

The memory 41 is realized by, for example, a semiconductor memory element such as a random access memory (RAM) or a flash memory, a hard disk, an optical disk, or the like. The memory 41 stores, for example, projection data and reconstructed image data.

The display 42 displays various types of information. For example, the display 42 displays medical images (CT images) generated by the processing circuit 44, a graphical user interface (GUI) for receiving various instructions from the operator, and the like. The display 42 is formed of, for example, a liquid crystal display (LCD), a cathode ray tube (CRT) display, or the like.

The input interface 43 receives various types of input from the operator. The input interface 43 converts the input into an electric signal, and outputs it to the processing circuit 44. For example, the input interface 43 receives collection conditions for collecting projection data, reconstruction conditions for reconstructing a CT image, image processing conditions for generating a post-processing image from the CT image, and the like from the operator. The input interface 43 is realized by, for example, a mouse, a keyboard, a trackball, switches, buttons, a joystick, or the like.

The processing circuit 44 controls the operation of the entire medical image diagnosis apparatus 1 according to the electric signal output from the input interface 43. The processing circuit 44 includes, for example, a system control function 441, an image generating/processing function 442, an image acquisition function 443, a data acquisition function 444, a display information generating function 445, and a display control function 446.

The system control function 441 controls various functions of the processing circuit 44 based on an input received from the operator through the input interface 43.

In the embodiment, the image generating/processing function 442 includes a preprocessing function, a reconstruction function, and an image processing function. The preprocessing function generates data by performing preprocessing such as logarithmic conversion, offset correction, inter-channel sensitivity correction, beam hardening correction, and the like on data output from the DAS 14. Note that data before preprocessing and data after preprocessing may sometimes be collectively referred to as "projection data".

The reconstruction function generates CT image data by reconstructing the projection data generated by the preprocessing function using a filtered back projection method, a successive approximation reconstruction method, or the like on.

The image processing function converts the CT image data generated by the reconstruction function into three-dimensional image data or tomographic image data of an arbitrary cross section by a known method based on an input received from the operator through the input interface 43.

The image acquisition function 443 acquires medical image data of a plurality of time phases. More specifically, the image acquisition function 443 acquires medical image data selected from medical image data generated by the image generating/processing function 442 based on selection operation by the operator.

Note that the image acquisition function 443 is an example of the image acquisition unit in the claims. Besides, "medical image data" and "medical image" are regarded herein as substantially the same. Therefore, in the following, the term "medical image data" sometimes refers to "medical image".

Based on medical image data of each time phase included in medical image data of a plurality of time phases acquired by the image acquisition function 443, the data acquisition function 444 acquires pixel value data contained in the medical image data. The pixel value data is acquired with respect to each region set by the operator. Since the medical image data is acquired at a plurality of time phases, the pixel value data is acquired with respect to each time phase. The data acquisition function 444 is an example of the data acquisition unit in the claims.

The display information generating function 445 generates display information based on the pixel value data of a plurality of time phases. The "display information" is, for example, information in which the pixel value data of a plurality of time phases is represented by a histogram of time. That is, the display information generating function 445 generates a histogram using image data of a plurality of time phases to indicate changes in the condition of the subject. The display information is generated with respect to each region set by the operator as described above. The display information generating function 445 is an example of the generation unit in the claims.

The display control function 446 displays a CT image (medical image) on the display 42 based on CT image data acquired by the image acquisition function 443. The display conditions of the medical image are set according to an input signal provided by the operator through the input interface 43.

The display control function 446 also displays the display information in a corresponding area of medical image data (representative image) of an arbitrary time phase. The display control function 446 displays the display information in a predetermined display range, and processes the display information in various display modes according to the conditions set by the operator. The display control function 446 is an example of the display control unit in the claims.

In addition to the above-described functions, the processing circuit 44 may have, for example, a scan control function. The scan control function controls the driving of each part of the gantry 10 according to various conditions of scanning (imaging of the subject) provided through the input interface 43.

A description has been given of the outline of the overall configuration of the medical image diagnosis apparatus 1 of the first embodiment. In the embodiment, the system control function 441, the image generating/processing function 442, the image acquisition function 443, the data acquisition function 444, the display information generating function 445, and the display control function 446 of the processing circuit 44 are realized by computer executable programs, which are stored in a memory circuit such as, for example, the memory 41. The processing circuit 44 is a processor that reads each of the programs from the memory circuit and executes it, thereby realizing a function corresponding to the program. In other words, having read the programs, the processing circuit 44 implements the functions illustrated in FIG. 1.

Although the functions of the processing circuit 44 (see FIG. 1) has been described as being realized by a single processor, it is not so limited. The processing circuit may be formed of a combination of a plurality of independent processors, each of which executes a program to realize corresponding one of the functions. Besides, the programs each corresponding to one of the functions are described as being stored in a single memory circuit (the memory 41); however, they can be stored in a plurality of memory circuits arranged in a distributed manner, and the processing circuit may read each of the programs from each of the memory circuits.

In the following, the image acquisition function 443, the data acquisition function 444, the display information generating function 445, and the display control function 446 of the processing circuit 44 will be described in further detail with reference to the drawings as appropriate.

First, the image acquisition function 443 acquires medical image data of a plurality of time phases. As the operator wants to know changes with time in the site to be diagnosed of the subject from the pieces of medical image data, it is necessary to generate display information that indicates the changes with time. For that purpose, the operator selects medical image data of a plurality of time phases as a reference to generate the display information. The processing circuit 44 acquires the medical image data selected by the operator using the image acquisition function 443.

The medical image data acquired is, for example, CT images. The medical image data contains position information indicating, for example, image position and image orientation, and size information indicating pixel size and the like. The size information is used to adjust the size of medical images of a plurality of time phases when the display information is generated based on the medical images. This is because, a medical image may sometimes be enlarged when reconstructed, and the image may be reconstructed over a wide area.

It is preferable to acquire medical images captured by medical image diagnosis apparatuses of the same type as the medical image data. This is because medical image data acquired by medical image diagnosis apparatuses varies depending on the types of the apparatuses. For example, CT image data acquired by the medical image diagnosis apparatus 1 (X-ray CT system) and MR image data acquired by MRI are different in the definition of pixel value data, and it is difficult to associate pixel value data of the CT image data with that of the MR image data (match the pixel values of the CT image and the MR image). However, medical images generated by different medical image diagnosis apparatuses can be used as long as their positions can be adjusted with their pixel values being matched.

As long as medical images to be compared are captured at the same position with respect to the same site to be diagnosed, the images need not necessarily be captured in one examination. For example, the medical images may be captured at different phases such as before contrast enhancement, arterial phase, venous phase, equilibrium phase, and the like in one examination, or may be captured in a series of treatments of the subject such as during examination, during treatment, and after treatment. The medical image data may also be contrast enhanced four-dimensional dynamic photographic image data.

When the operator selects the medical image data of a plurality of time phases as a reference to generate the display information, the examination list of the subject is displayed on the display 42. The operator selects medical images that he/she think are necessary from the examination list. The medical images can be selected in any manner. For example, the medical images may be selected with respect to each study (examination), with respect to each series in one study, or the medical images may be selected from those of a specific series. The medical images may also be selected from a plurality of studies or series.

Having acquired the medical image data of a plurality of time phases by the image acquisition function 443, the processing circuit 44 arranges the medical images in chronological order using the image acquisition function 443. The processing circuit 44 also adjusts the positions of the medical images.

In order to generate a histogram as the display information, medical images of almost the same position including the site to be diagnosed are acquired. Nevertheless, there may be a misalignment in the positions of the medical images. Therefore, prior to generating the histogram, the medical images are aligned with each other such that the region whose pixel value data is to be acquired is located in the same position in all the medical images.

The operator selects representative image data (hereinafter referred to as "representative image") from the medical image data selected through the input interface 43. The representative image illustrates the site to be diagnosed. When a histogram is generated as the display information (described later), the histogram is displayed on the representative image. That is, the representative image serves as the basis for displaying the histogram, and illustrates the region whose changes are indicated by the histogram. The processing circuit 44 acquires a corresponding representative image based on a selection made by the operator using the image acquisition function 443, and displays it on the display 42.

Figure 2:
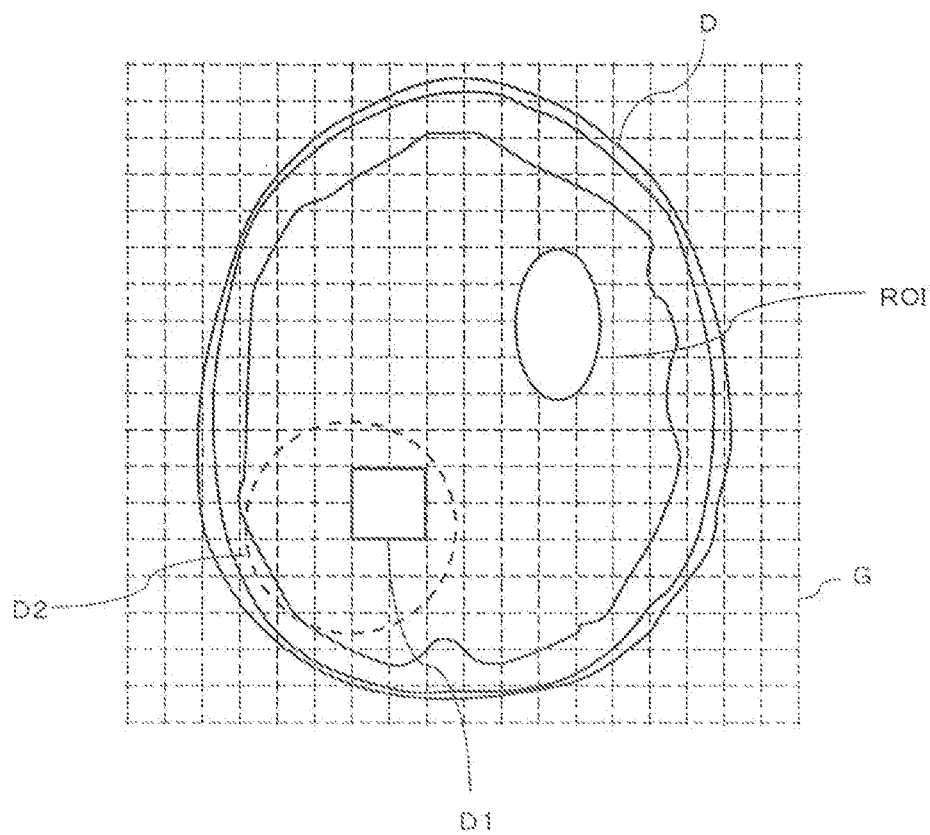
FIG. 2 is a schematic diagram illustrating a target image for setting a region to generate a histogram according to the embodiment.

The processing circuit 44 sets a region necessary for generating the display information using the representative image by the data acquisition function 444. FIG. 2 is a schematic diagram illustrating a representative image D for setting a region for generating a histogram in the embodiment. Incidentally, the representative image D of FIG. 2 is displayed on the display 42 (not illustrated in FIG. 2). The operator sets conditions necessary for generating the display information while viewing the representative image D displayed on the display 42.

While FIG. 2 illustrates an axial cross-sectional image as the representative image D, it is not so limited. The representative image D may be, for example, a coronal cross-sectional image, a sagittal cross-sectional image, or an oblique cross-sectional image created by multi planar reconstruction (MPR).

In FIG. 2, the representative image D is displayed as being superimposed on a grid G (squares). The grid G is used for setting a target region upon generating a histogram as the display information. With respect to the unit of histogram generation, for example, a square of the grid G may be set as a target region, or a plurality of squares may be collectively set as one target region.

The size of the grid G is not fixed, and the size of one square can be arbitrarily increased and decreased. When the grid G is set to be finest, one square can be set as one pixel.

Besides, an arbitrary region may be set for generating a histogram without using the grid G. For example, in the representative image D of FIG. 2, a region of interest (ROI) is set on the right side of the approximate center. A histogram may be generated for only this region. It is also possible that a histogram is not to be generated only for the region set as ROI. The shape of the ROI can be arbitrarily set.

Further, a plurality of regions may be set. In this case, priorities are assigned to the regions, and whether to generate a histogram is determined with respect to each of the regions according to the priorities.

For example, FIG. 2 illustrates a square region D1 and a region D2, which is indicated by a broken line and includes the square region D1, in the lower left of the representative image D. The representative image D is divided into regions by the grid G.

In this case, for example, the operator designates the region D2 as a region for which a histogram is not to be generated, and the region D1 in the region D2 as a region for which a histogram is to be generated. With this, histograms are generated for the region D1 as well as other regions than the region D2 defined by the squares of the grid G.

Further, a threshold may be set to determine whether to generate a histogram without setting ROI in the representative image D. In this case, a histogram is generated or not generated depending on, for example, whether the pixel value is within the threshold.

As described above, whether to generate a histogram can be set by using an arbitrary region in addition to the grid G. Thus, whether to generate a histogram can be set with respect to each of divided regions such as, for example, the inside of the tumor and the surrounding tissue.

In this manner, the processing circuit 44 sets regions for generating a histogram of each of them by the data acquisition function 444. Having completed the setting of the regions, the processing circuit 44 acquires pixel value data with respect to each of the regions from all the medical images of a plurality of time phases acquired. The processing circuit 44 generates a change curve in the regions by using the pixel value data of all the medical images of a plurality of time phases.

Figure 3:
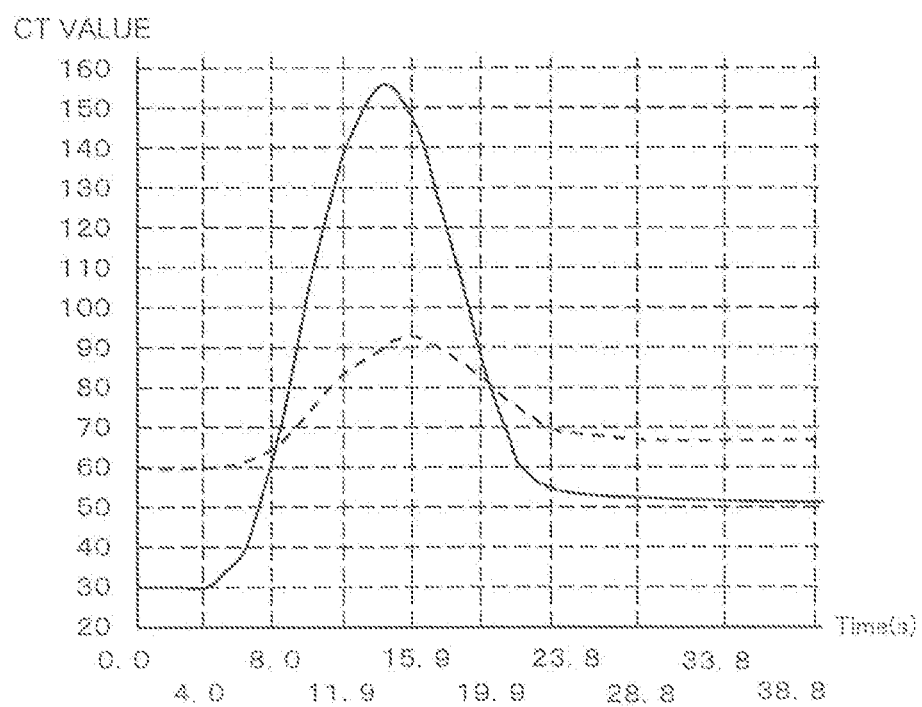
FIG. 3 is a graph illustrating pixel value data of a plurality of time phases as change curves according to the embodiment.

FIG. 3 is a graph illustrating the pixel value data of a plurality of time phases as change curves in the embodiment. The change of the pixel value data in the medical image data of a plural time phases indicates the change of the concentration of contrast agent in each of the regions when the examination is performed on the subject using the contrast agent. In the graph illustrated in FIG. 3, the vertical axis represents pixel value data (CT value), and the horizontal axis represents time (Time(s)).

FIG. 3 illustrates changes in two pieces of pixel value data (numerical values, graphs are schematically expressed) for the sake of explanation. The solid line indicates the change of the pixel value data of the artery, and the broken line indicates the change of the pixel value data of the tissue.

Looking at the change of the pixel value data of the artery indicated by the solid line in FIG. 3, the CT value is 30 at the beginning (time 0), and it does not change substantially for 4.0 seconds. Then, the CT value rapidly rises to over 150 after almost 15.9 seconds. However, the CT value drops quickly, and after 23.8 seconds, it is below 60. The CT value generally drops to around 50 until the end (time 38.8).

Next, looking at the change of the pixel value data of the tissue indicated by the broken line, the graph rises and falls gently as a whole compared to the pixel value data of the artery. At the beginning, the CT value is about 60 at first, and even the peak value just slightly exceeds 90. Although the CT value drops, it is maintained at a value slightly below 70. As can be seen in FIG. 3, the peak time is slightly later than that of the pixel value data of the artery.

As illustrated in the graph of FIG. 3, the CT values are different at the beginning (time 0) between the pixel value data of the artery and that of the tissue. In this state, histograms generated for the regions cannot be compared. Therefore, the change curves of these pieces of pixel value data are reset such that the CT values are adjusted to "0" at the beginning (time 0) irrespective of the regions.

Figure 4:
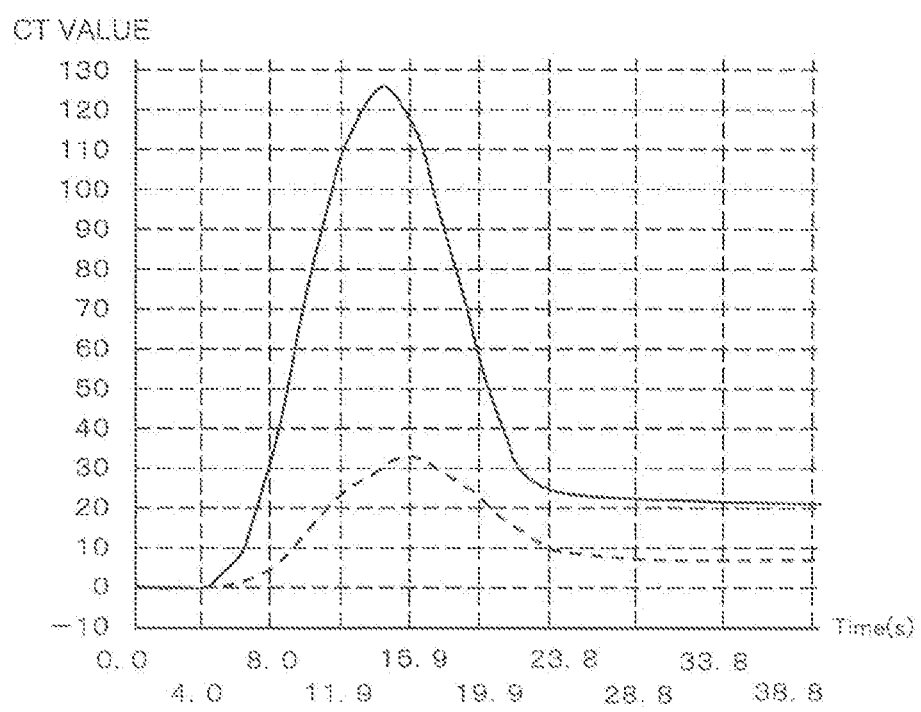
FIG. 4 is a graph in which the positions of the change curves illustrated in FIG. 3 are adjusted according to the embodiment.

FIG. 4 is a graph in which the positions of the change curves illustrated in FIG. 3 are adjusted in the embodiment. Both the CT values of the pixel value data of the artery and that of the tissue are set to "0" at the beginning (time 0). For example, by setting the CT value before contrast enhancement to "0", only the change after contrast enhancement can be represented in the histogram. As a result, it is possible to appropriately figure out how the pixel value data of the artery and that of the tissue change over the same time after contrast enhancement. This process is performed on all the pixel value data of the medical images of a plurality of time phases acquired.

After acquiring the pixel value data of the medical images of a plurality of time phases using the data acquisition function 444 and adjusting the positions of the images as described above, the processing circuit 44 generates display information (histogram).

The processing circuit 44 generates a histogram for each of the regions using the display information generating function 445. First, the processing circuit 44 divides the pixel value data (CT values) into a plurality of ranges, and sets a different display mode with respect to each of the ranges.

Figure 5:
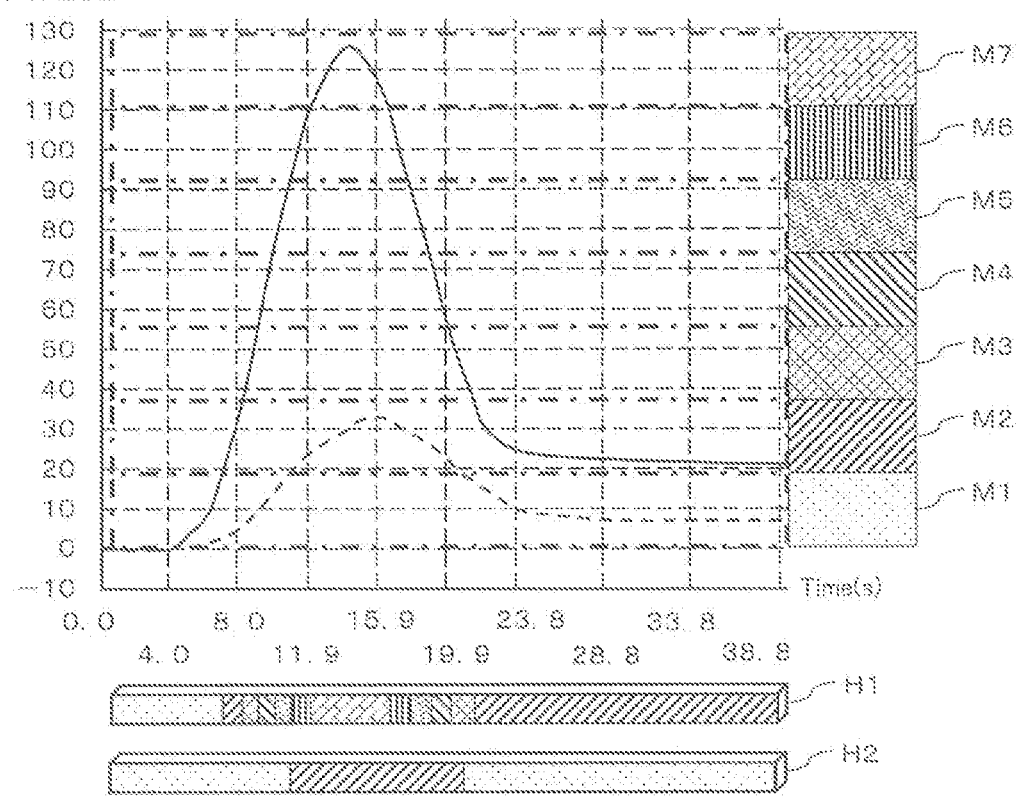
FIG. 5 is a schematic diagram for explaining how to generate a histogram of each of the change curves by dividing pixel values into a plurality of ranges according to the embodiment.

FIG. 5 is a schematic diagram for explaining how to generate a histogram of each of the change curves by dividing pixel values into a plurality of ranges in the embodiment. FIG. 5 illustrates the change curves representing the pixel value data of the artery and that of the tissue illustrated in FIG. 4. Both the CT values (pixel value data) are set to "0" at the beginning (time 0).

A plurality of ranges are illustrated on the graph by alternate long and short dashed lines. For example, a CT value range from 0 to a little less than 20 is illustrated at the bottom. Further, a CT value range from a little less than 20 to a little less than 40 is illustrated as an upper range. In total, seven CT value ranges are provided from 0 to 130. The number of CT value ranges may be arbitrarily determined.

Seven patterns M1 to M7 are illustrated on the right side of the graph, each for one of the CT value ranges. The patterns are each assigned to one of the ranges on the left side of them. Specifically, the pattern M1 is assigned to the CT value range from 0 to a little less than 20. The pattern M2 is assigned to the CT value range from a little less than 20 to a little less than 40. The pattern M3 is assigned to the CT value range from a little less than 40 to the middle of 50 to 60. The pattern M4 is assigned to the CT value range from the middle of 50 to 60 to the middle of 70 to 80. The pattern M5 is assigned to the CT value range from the middle of 70 to 80 to a little greater than 90. The pattern M6 is assigned to the CT value range from a little greater than 90 to around 110. The pattern M7 is assigned to the CT value range from around 110 to 130.

Further, below the graph, two columns are illustrated extending horizontally under the numerals indicating the time on the horizontal axis. The upper column represents the pixel value data of the artery indicated by the solid line in the graph as a histogram. The lower column represents the pixel value data of the tissue indicated by the broken line in the graph as a histogram. In the following, for the sake of explanation, the upper column is referred to as "histogram H1", while the lower column is referred to as "histogram H2".

Described below is the generation of the histogram H2. The processing circuit 44 generates a histogram using the display information generating function 445. First, the value (CT value) of the pixel value data of the tissue indicated by the broken line in the graph and the ranges thereof are checked. As described above, the CT value range from 0 to a little less than 20 is illustrated by alternate long and short dashed lines at the bottom.

At the beginning (time 0), the CT value (pixel value data) of the tissue is 0. The CT value gradually increases, and reaches a value a little less than 20, which is the upper limit value of the lowest range, after the lapse of about 10 seconds. The display information generating function 445 prepares a column indicating the length of time from 0 to 10 seconds, and applies the dot pattern M1 to the column.

Looking further at the pixel value data of the tissue, the CT value exceeds 20 after the lapse of 10 seconds, and reaches its peaks at the lapse of about 15.9 seconds. Thereafter, the CT value decreases. Then, the CT value falls below the value a little less than 20 after the lapse of around 20 seconds. As described above, the CT value is over 20 after the lapse of 10 to 20 seconds and is in the next range, which is assigned the pattern M2 on the right side of the graph. The display information generating function 445 prepares a column indicating the length of time from 10 to 20 seconds, and applies the pattern M2 to the column.

The display information generating function 445 checks the change of the pixel value data after the lapse of 20 seconds. Referring to FIG. 5, after falling below 20 at the lapse of 20 seconds, the CT value is maintained at a value a little less than 10 until the end at the lapse of 38.8 seconds. After the lapse of 20 seconds, the CT value is in the lowest range. The display information generating function 445 prepares a column indicating the length of time from 20 seconds to the end, and applies the pattern M1 to the column. Then, the display information generating function 445 arranges these patterned columns along the line of time such that they are displayed as one column. This column is the histogram H2 illustrated in FIG. 5.

With this process, the change curve of the pixel value data of the tissue can be reflected on the column. The length of the column indicates the lapse of time, and the pattern applied to each of the columns indicates a range of the pixel value data (CT value). With reference to the histogram H2, the change of the pixel value data (CT value) over time can be figured out easily and reliably.

The histogram H1 illustrated in FIG. 5 is similarly generated by the above-described process of the display information generating function 445 to the pixel value data of the artery. The fluctuation range of the pixel value data of the artery is larger as compared to that of the pixel value data of the tissue, and the CT value moves over more ranges. To be specific, the CT value moves over all the ranges. Therefore, differently from the histogram H2 of the pixel value data of the tissue, the histogram H1 indicates the change of the pixel value data with all the patterns M1 to M7.

By the generation process of the display information generating function 445 described above, the change of the pixel value data over time is represented in the histogram. The above description has been given referring to FIGS. 4 and 5 each illustrating a graph of changes in pixel value data with respect to each of the regions for the sake of convenience; however, the graphs is not necessarily required for the display information generating function 445 to generate a histogram. Besides, in order to describe that the histogram represents the lapse of time and the change of pixel value data, the columns (histograms) are illustrated horizontally along the time axis in FIG. 5; however, such display is also not required upon generation of the histogram.

For convenience of illustration, the histograms are provided with the patterns M1 to M7 each corresponding to one of the ranges of pixel value data; however, the change of the pixel value data need not necessarily be represented by patterns, and it may be represented by color, for example. Further, the display mode of the histogram such as, for example, patterns or colors to be used and the assignment of them to the ranges of pixel value data, can be arbitrarily set.

Upon completion of the generation of the histograms H1 and H2, the processing circuit 44 combines the histograms with the representative image D, and displays it on the display 42 using the display control function 446.

Figure 6:
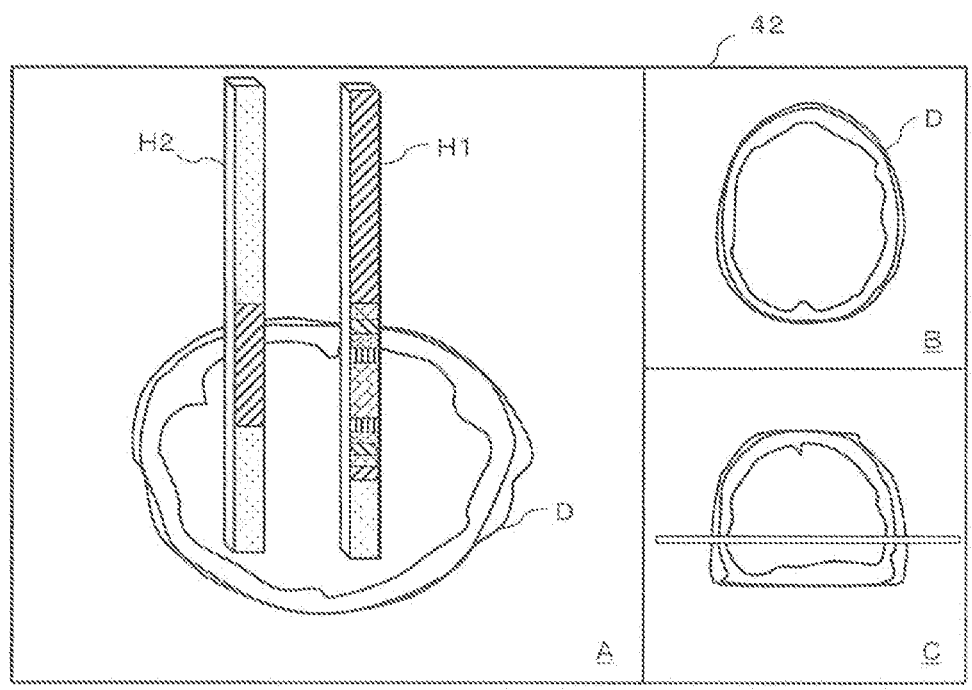
FIG. 6 is an example of a screen displaying histograms combined with a representative image according to the embodiment.

FIG. 6 is an example of a screen displaying the histograms H1 and H2 combined with the representative image D in the embodiment. In FIG. 6, the screen of the display 42 is divided into three regions, and the histograms H1 and H2 combined with the representative image D are displayed in the largest region A.

The right side of the screen is divided into upper and lower regions, and the representative image D is displayed in the upper region B. Further, an image that indicates the position where the representative image D is taken is displayed in the lower region C. The representative image D is taken along a line extending across the tomographic image displayed in the region C. The layout on the display 42 is not limited to that illustrated in FIG. 6 or any other drawings, and any display layout can be used.

As described above, the histograms H1 and H2 combined with the representative image D are displayed in the region A on the screen of the display 42. The two histograms H1 and H2 are each arranged at a position indicated by the pixel value data represented in each of the histograms in the representative image D. Accordingly, for example, the position of, the histogram H1 corresponds to the region where the pixel value data represented in the histogram H1 is acquired. In FIG. 6, the lapse of time is indicated from the bottom to the top of the histograms H1 and H2 that are displayed vertically. The patterns indicate the change of the pixel value data.

Figure 7:
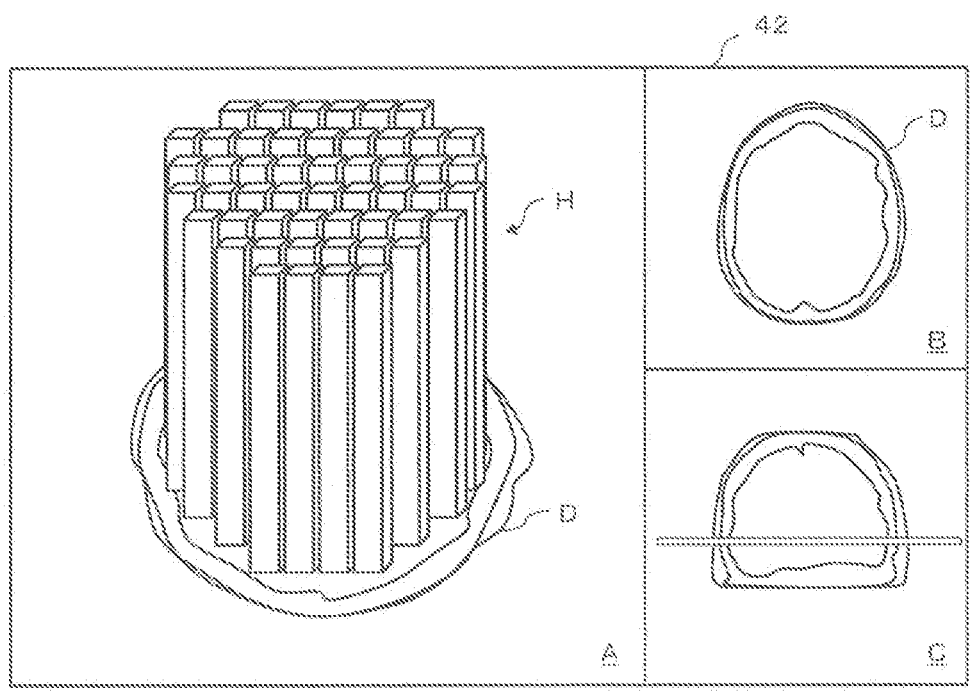
FIG. 7 is an example of a screen displaying histograms combined with a representative image according to the embodiment.
Figure 8:
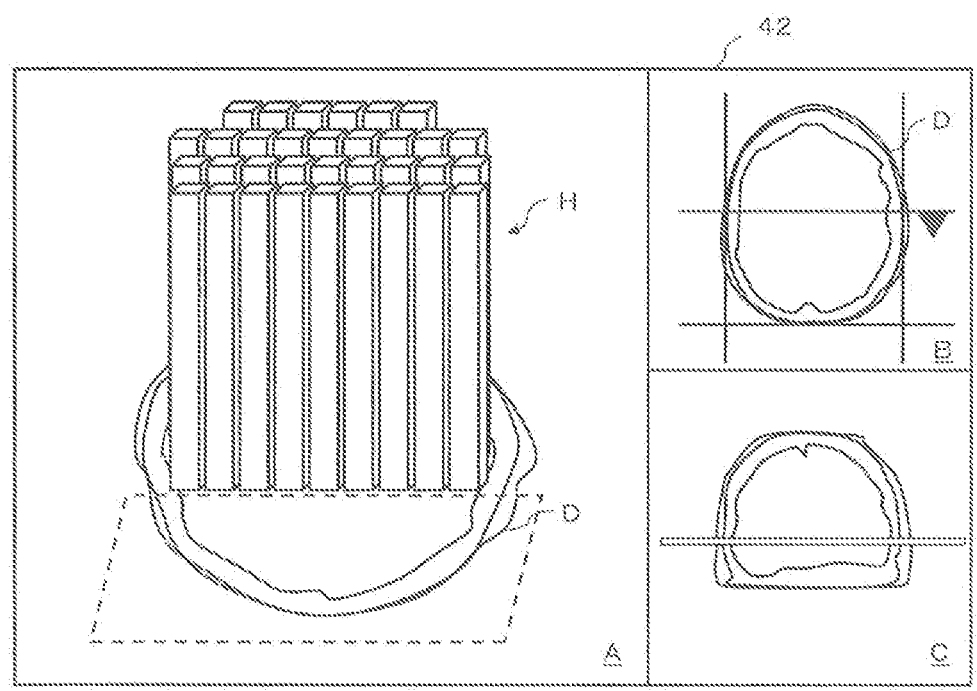
FIG. 8 is an example of a screen displaying histograms combined with a representative image according to the embodiment.
Figure 9:
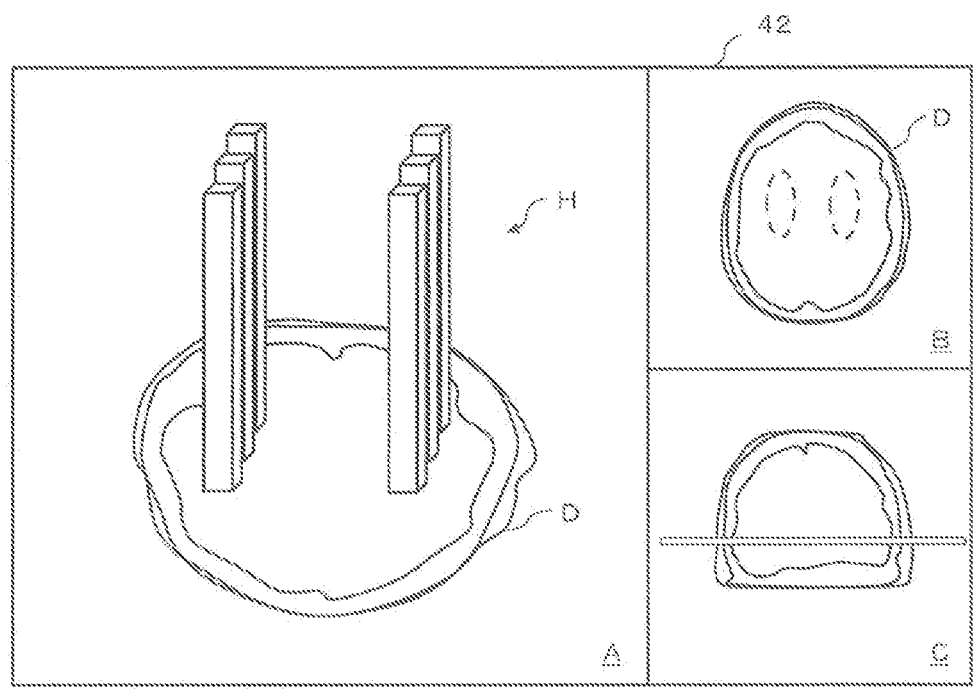
FIG. 9 is an example of a screen displaying histograms combined with a representative image according to the embodiment.

The processing circuit 44 is capable of displaying a composite image of the histograms H and the representative image D on the display 42 in various manners using the display control function 446. FIGS. 7 to 9 illustrate examples of the screen displaying a composite image of histograms and the representative image in the embodiment. In the following, a plurality of histograms illustrated in FIGS. 7 to 9 are collectively referred to as "histograms H". The patterns for indicating the change of pixel value data over time represented in the histograms H are omitted in FIGS. 7 to 9.

In the region A of the display 42 illustrated in FIG. 7, a plurality of histograms H, each generated for one of the regions, are displayed in the representative image D. This display example represents the case where the regions for generating the histograms H are set using the grid G.

However, if the histograms H of all the regions are displayed on the display 42 as illustrated in FIG. 7, the operator cannot view changes in the pixel value data of some of the histograms H displayed, for example, at the back of the screen of the display 42.

Therefore, the operator performs an operation for displaying the histograms H to be viewed. As an example of the operation, it is possible to the composite image of the histograms H and the representative image D displayed in the region A. The operator can freely rotate the composite image through the input interface 43. The composite image can be rotated not only in the horizontal direction but also with an angle so that, for example, the histograms H can be seen obliquely from above.

As an example of the operation, the following can be cited. The representative image D is displayed in the region B of the display 42. The representative image D may be used to set the display regions of the histograms H in the region A.

Referring to FIG. 8, four lines are overlaid on the representative image D in the region B displayed on the display 42. These lines serve as a tool for setting the range of the histograms H to be hidden. A downward arrow is displayed on one of the lines that extends horizontally at substantially the center of the representative image D. The arrow means that, as indicated by the direction of the arrow, the histograms H below the line, i.e., the histograms H at the front of the screen in the representative image D in the region A, are not displayed. The operator moves these lines appropriately to hide some of the histograms H so that he/she can view desired ones of the histograms H.

The display control function 446 of the processing circuit 44 hides the display of the histograms H in a designated region in response to the operator's operation of moving the line through the input interface 43. FIG. 8 illustrates the region A of the display 42 in this state. In FIG. 8, the hidden region is indicated by a broken line. Since the histograms H are not displayed on the front side in the region A of the display 42, those on the back side, i.e., the histograms H of the region above the line set by the operator in the region B, are displayed on the foreground. The operator can display desired ones of the histograms H by this operation.

While a region to be hidden is designated in this example, the operator may designate a region to be displayed. In addition, the operator can make the show or hide setting after rotating the composite image of the histograms H and the representative image D.

Further, the operator can display only desired ones of the histograms H. For example, as illustrated in FIG. 9, the operator sets an arbitrary display range using the representative image D in the region B of the display 42. The display range may be set by surrounding a region to be displayed with a circle as illustrated in FIG. 9 (in the example of FIG. 9, two regions are each surrounded by an ellipse). The display range may be set with any other shape. There may be a single region or a plurality of regions to be displayed. Referring to FIG. 9, only the histograms H in the display range, which is set by using the representative image D in the region B, are displayed in the region A of the display 42.

Next, the display mode of the histograms H will be described with reference to FIGS. 10 to 13. FIGS. 10 to 13 illustrate examples of the display mode of the histograms H in the embodiment.

Figure 13:
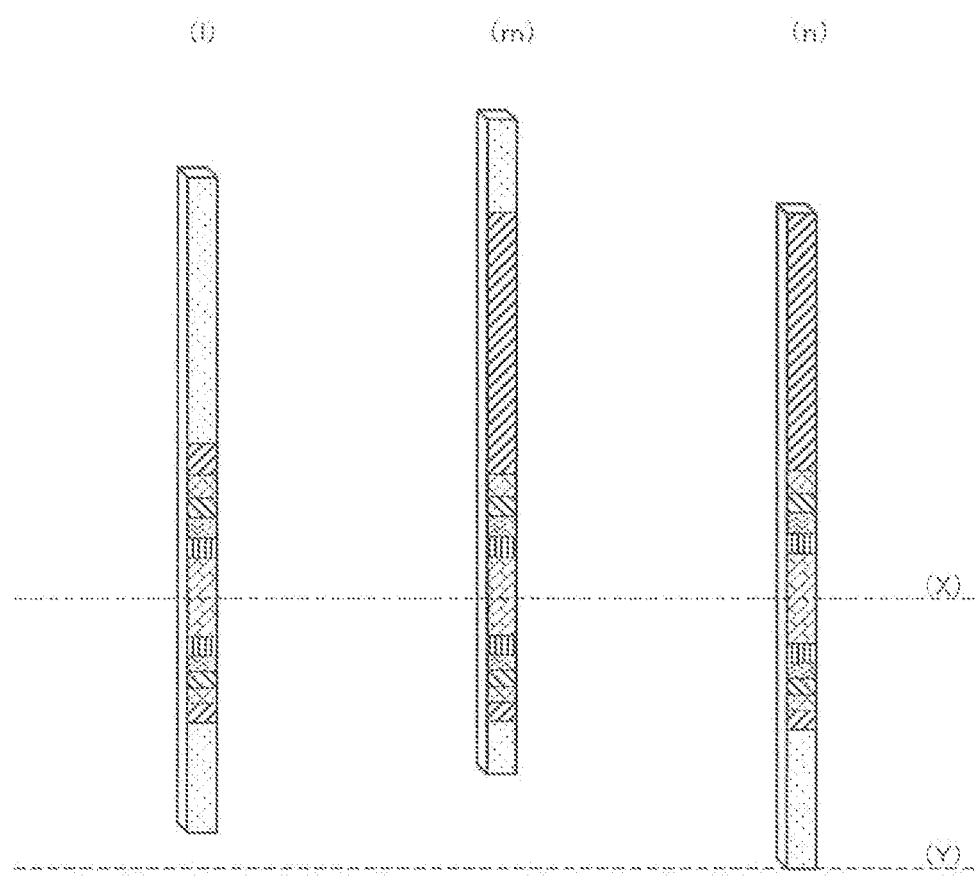
FIG. 13 is a schematic diagram illustrating an example of the display mode of the histogram according to the embodiment.

In the figures except FIG. 13, the histograms H are displayed on the representative image D indicated by an ellipse. The lapse of time is indicated from the bottom to the top of the histograms H, and the patterns represent the change of the pixel value data. The correspondence between the patterns and the ranges of the pixel value data is as illustrated in FIG. 5. Note that, although the content indicated by the histograms H will be described below, it is only one perspective and interpretation, and the histograms H need not necessarily indicate such content.

Figure 10:
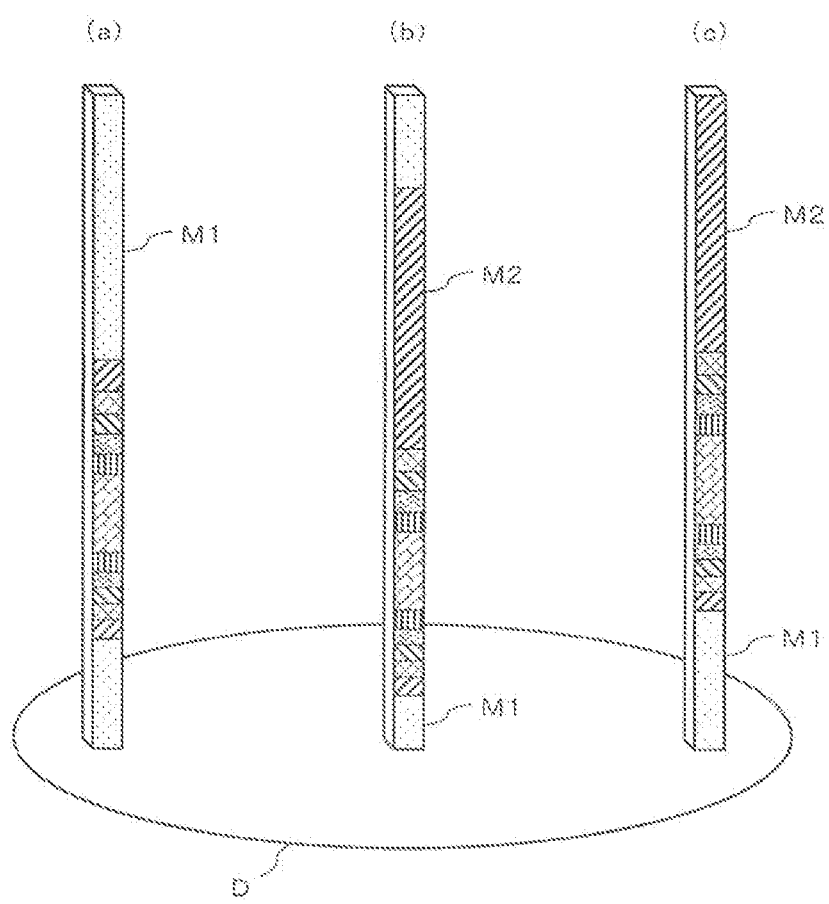
FIG. 10 is a schematic diagram illustrating an example of the display mode of the histogram according to the embodiment.

FIG. 10 illustrates three histograms (a) to (c). As described above, the histograms H represent changes in pixel value data over time. For example, in the histogram (a), the area of the pattern M1 corresponding to a low CT value range is larger as compared to the histograms (b) and (c). This indicates that the contrast agent stains and exits rapidly because the part enhanced by the contrast agent has a high CT value.

In the case of the histogram (b), a range of time indicated by the pattern M1 corresponding to a low CT value range at the bottom is small. This indicates that the contrast agent requires a short time to stain. However, a range of time indicated by the pattern M2, which is the second pattern from the top in the histogram (b), is large. Since the part enhanced by the contrast agent has a high CT value as described above, this indicates that the contrast agent takes a long time to exit after it stains. In the case of the histogram (c), a range of time indicated by the pattern M1 at the bottom is large, and also a range of time indicated by the pattern M2 at the top is large. This indicates that the contrast agent takes a long time to stain and exit.

Figure 11:
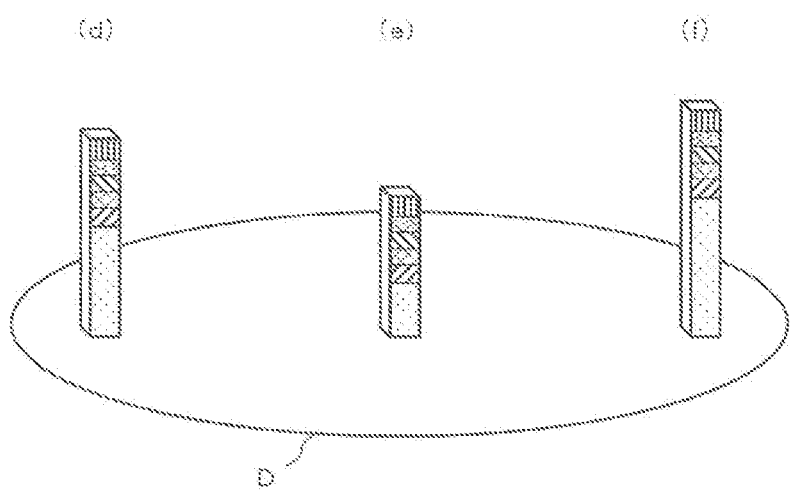
FIG. 11 is a schematic diagram illustrating an example of the display mode of the histogram according to the embodiment.

FIG. 11 illustrates three histograms (d) to (f), which represent the time taken until the CT value (pixel value data) falls within a maximum value range and the change of the pixel value data until the CT value reaches the maximum value range. The shorter the length of the histograms H, the faster the CT value falls within the maximum value range. Looking at the histograms (d) to (f) illustrated in FIG. 11, the histogram (e) in the middle is the shortest. This indicates that, among the regions represented by the histograms (d) to (f), the CT value reaches the maximum value range first in the region of the histogram (e).

Figure 12:
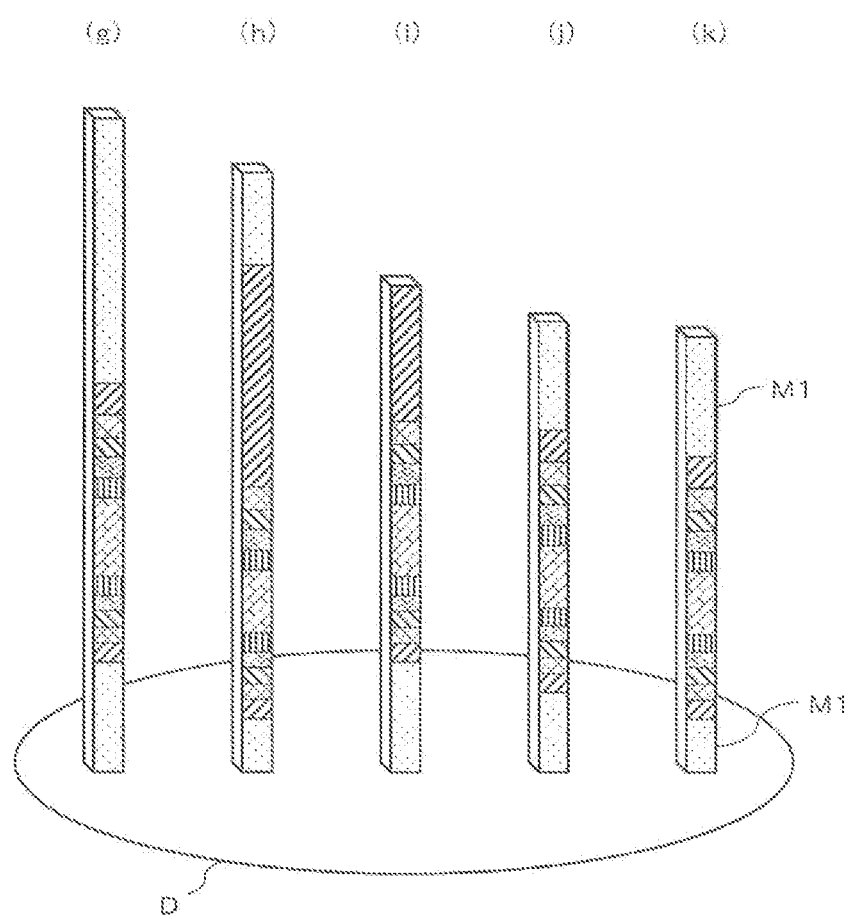
FIG. 12 is a schematic diagram illustrating an example of the display mode of the histogram according to the embodiment.

FIG. 12 illustrates histograms (g) to (k), each representing the time during which the regions are stained with the contrast agent. The histograms (g) to (k) are arranged in descending order of their heights. An increase in the height of the histograms indicates that the contrast agent takes a longer time to exit after entry. That is, the tallest histogram (g) indicates that the contrast agent requires the longest time to exit, and the contrast agent exits faster as the heights of the histograms decrease toward the histogram (k).

The histograms (j) and (k) have about the same height, which means that the contrast agent exits at substantially the same speed as the height of the histograms indicates the time taken until the contrast agent exits. Since the pattern M1 at the top of the histogram (k) is longer than that of the histogram (j), it can be assumed that the contrast agent requires a longer time to exit as compared to the histogram (j). On the other hand, the pattern M1 at the bottom of the histogram (k) is short, which indicates that the contrast agent stains in a short time. Consequently, the histogram (k) is shorter than the histogram (j), and it can be considered that the contrast agent exits faster as a whole as compared to the case of the histogram (j).

FIG. 13 illustrates histograms (1) to (n) with lines X and Y. The line X indicates a position where the CT value (pixel value data) is maximum. The representative image D is not illustrated in FIG. 13.

When the histograms are displayed on the representative image D as, for example, the histograms (a) to (c) illustrated in FIG. 10, the lower parts of the histograms are displayed as being aligned on the representative image D. In FIG. 13, the position of the maximum CT value is indicated by the line X, and all the histograms (1) to (n) are displayed such that the time at which the CT value reaches the maximum value is placed on the line X. In this case, the lower parts of the histograms are not aligned at the position of the representative image D as illustrated in FIG. 10. As a result, the histograms are displayed unevenly.

In this example, the line Y is displayed using the bottom of the histogram (n) as a reference, and the histograms (1) and (m) are displayed above the line Y. It is possible to figure out the time taken until the CT value reaches the maximum value from the distance between the line Y and each of the histograms displayed above the line Y. In FIG. 13, the bottom of the histogram (m) is farthest away from the line Y, which indicates that the region represented by the histogram (m) is stained with the contrast agent easily compared to the regions of the other histograms (1) and (n).

The three histograms (1) to (n) illustrated in FIG. 13 are displayed without adjusting their heights as those illustrated in, for example, FIGS. 11 and 12. Therefore, the entire time course of the pixel value data in the regions can be displayed together with how well the contrast agent stains.

Besides, the display of a histogram can be hidden depending on the region for which the histogram is generated such as, for example, a region corresponding to a bone portion where the pixel value data does not change or the like. In this case, for example, the operator may hide the display of each histogram while viewing the histograms displayed on the display 42, or the histogram that is assigned a single pattern (i.e., with no change in the pixel value data) may be hidden automatically.

The processing circuit 44 may generate a histogram by using the display information generating function 445 each time the data acquisition function 444 acquires pixel value data of a plurality of time phases. When a region for which a histogram is to be generated is set in advance, and, each time medical image data is acquired, the medical image data is reflected in the histogram, the change of the pixel value data can be reflected in the histogram in real time. In this case, the histogram is displayed as if it is extending on the display 42.

[Operation]

Next, with reference to FIGS. 14 to 17, a description will be given of the operation of the medical image diagnosis apparatus 1 for generating histograms.

Figure 14:
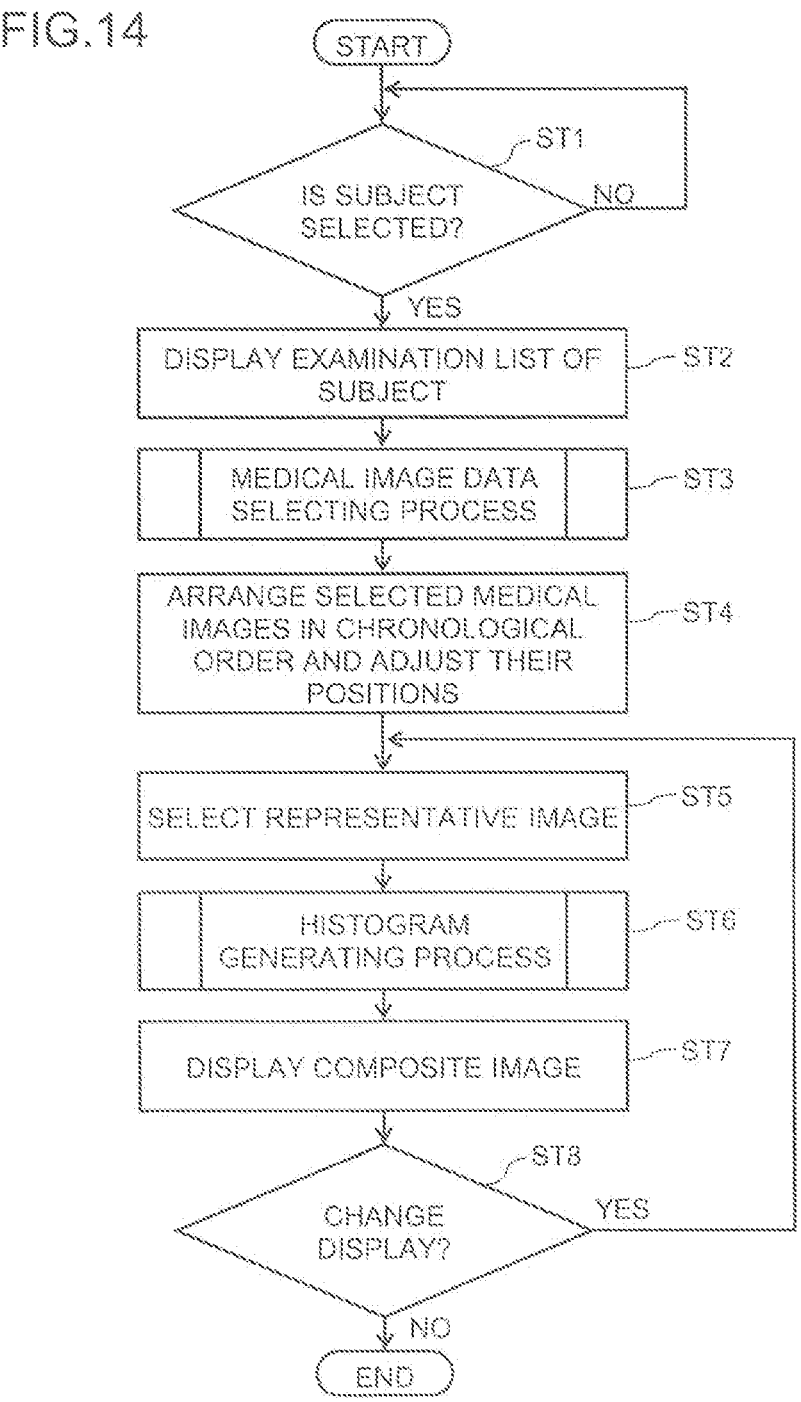
FIG. 14 is a flowchart schematically illustrating the process from the generation of histograms to the display of a composite image of the histograms and a representative image according to the embodiment.

FIG. 14 is a flowchart schematically illustrating the process from the generation of histograms to the display of a composite image of the histograms and a representative image in the embodiment. It is assumed herein that the medical image diagnosis apparatus 1 has acquired medical image data related to the subject to be examined for generating histograms.

Specifically, the processing circuit 44 generates a medical image (CT image) from projection data using the image generating/processing function 442, and stores it in, for example, the memory 41. The medical image data need not necessarily be stored in the memory 41 of the medical image diagnosis apparatus 1, and it may be stored in, for example, an image storage server or the like connected to a communication network that the medical image diagnosis apparatus 1 can be connected to.

As illustrated in FIG. 14, in order to check changes in the CT value (pixel value data) of the site to be diagnosed with histograms, the operator starts the generation of histograms. First, the processing circuit 44 displays, for example, a list of subjects to be examined on the display 42 using the display control function 446 (step ST1).

When the operator does not select one of the subjects (NO in step ST1), the processing circuit 44 is on standby. On the other hand, when the operator selects one of the subjects from the list through the input interface 43 (YES in step ST1), the processing circuit 44 displays a list of examinations performed on the subject on the display 42 (step ST2).

Although the subject is described as being selected by the operator from a list of subjects displayed on the display 42, for example, the operator may enter ID or the like of the subject directly into the medical image diagnosis apparatus 1 to select the subject.

Figure 15:
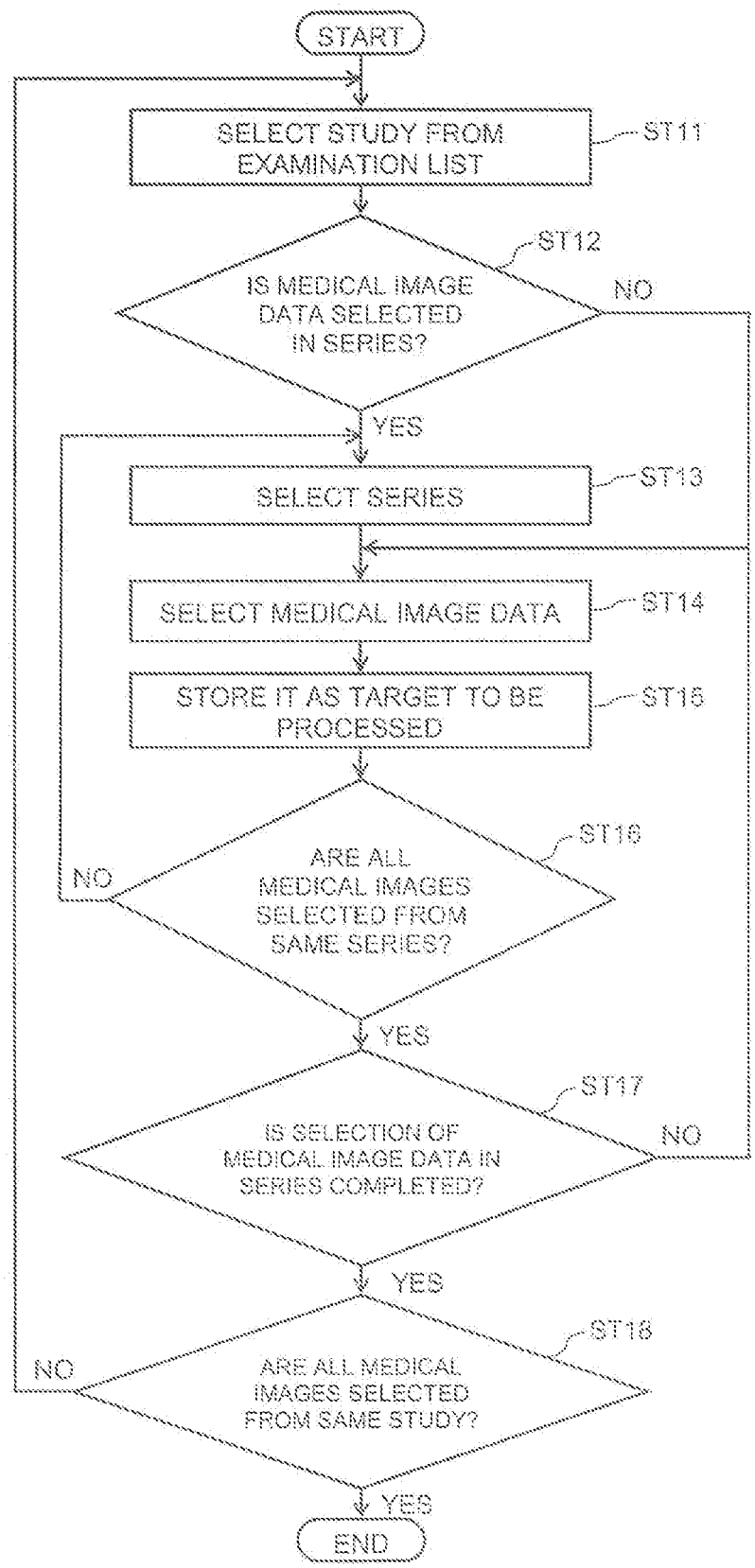
FIG. 15 is a detailed flowchart of a medical image data selecting process in the flowchart of FIG. 14 according to the embodiment.

When the examination list is displayed on the display 42, the operator selects medical image data to be used for generating the histograms from the examination list (step ST3). The processing circuit 44 acquires the medical image data selected by the operator using the image acquisition function 443. FIG. 15 is a detailed flowchart of the medical image data selecting process in the flowchart of FIG. 14.

For example, the examination list displayed on the display 42 indicates studies (examinations), series, and individual medical image data. First, the operator selects a study from the examination list (step ST11 in FIG. 15). Next, for example, the display 42 displays options for determining whether to select medical image data in a series included in the study (step ST12). The operator selects whether to select a series (YES in step ST12) or not (NO in step ST12) from the options.

Having received a signal indicating that the operator has determined to select medical image data in a series through the input interface 43, the processing circuit 44 selects medical image data in the series (step ST13). Then, in response to a signal indicating the selection of medical image data included in the series (step ST14), the processing circuit 44 acquires the medical image data stored in, for example, the memory 41.

On the other hand, having received a signal indicating that the operator has determined not to select medical image data in a series, the processing circuit 44 receives the selection of medical image data directly from the operator (step ST14). The processing circuit 44 acquires the medical image data stored in, for example, the memory 41.

The processing circuit 44 stores the medical image data selected by the operator and acquired from the memory 41 or the like as, for example, a target to be processed for generating histograms (step ST15).

The medical images selected by the operator may be stored collectively as medical image data acquired by a series of selections in, for example, the memory 41. If the medical images are collectively acquired from the memory 41 according to the operator's selection after completion of selection of all the medical images, for example, the display 42 may display the medical images in such a manner as to clearly indicate that they have been selected.

Subsequently, the processing circuit 44 checks whether the operator selects all medical images from the same series (step ST16). When the operator specifies to select medical images included in another series (NO in step ST16), the process returns to step ST13, and the series selection process is performed again.

On the other hand, when all the medical images to be selected are included in the same series (YES in step ST16), the processing circuit 44 displays an inquiry on the display 42 as to whether the selection of medical image data in the series has been completed (step ST17).

When the selection of medical image data in the series has not been completed (NO in step ST17), the process returns to step ST14 to further select medical image data. On the other hand, when the selection of medical image data in the series has been completed (YES in step ST17), the processing circuit 44 displays an inquiry as to whether all medical images are selected from the same study (step ST18).

When medical image data is further selected from another study (NO in step ST18), the process returns to step ST11 to further select a study. On the other hand, when the selection of medical image data in the study/studies has been completed (YES in step ST18), the medical image data selecting process ends.

Referring back to FIG. 14, the processing circuit 44 arranges the selected medical images in chronological order and adjusts their positions (step ST4). The processing circuit 44 performs this process as a preparation for generating histograms using the selected medical image data of a plurality of time phases so that the medical image data can be appropriately used as described above.

After that, the operator selects a representative image from the medical images (step ST5). The processing circuit 44 recognizes the selected one of the medical images as a representative image and uses it in the process of generating histograms. Then, the process proceeds to the histogram generating process (step ST6).

Figure 16:
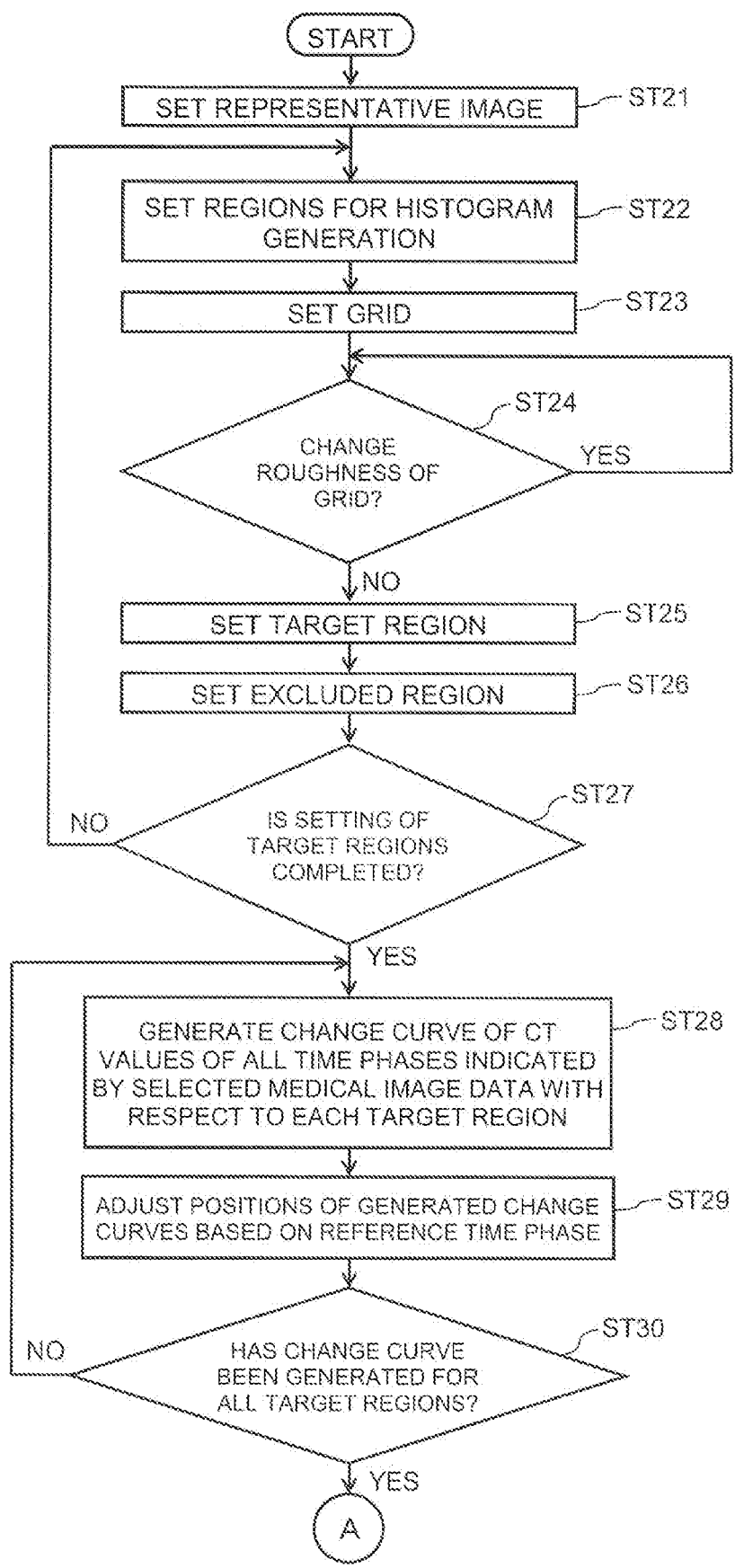
FIG. 16 is a detailed flowchart of a histogram generating process in the flowchart of FIG. 14 according to the embodiment.
Figure 17:
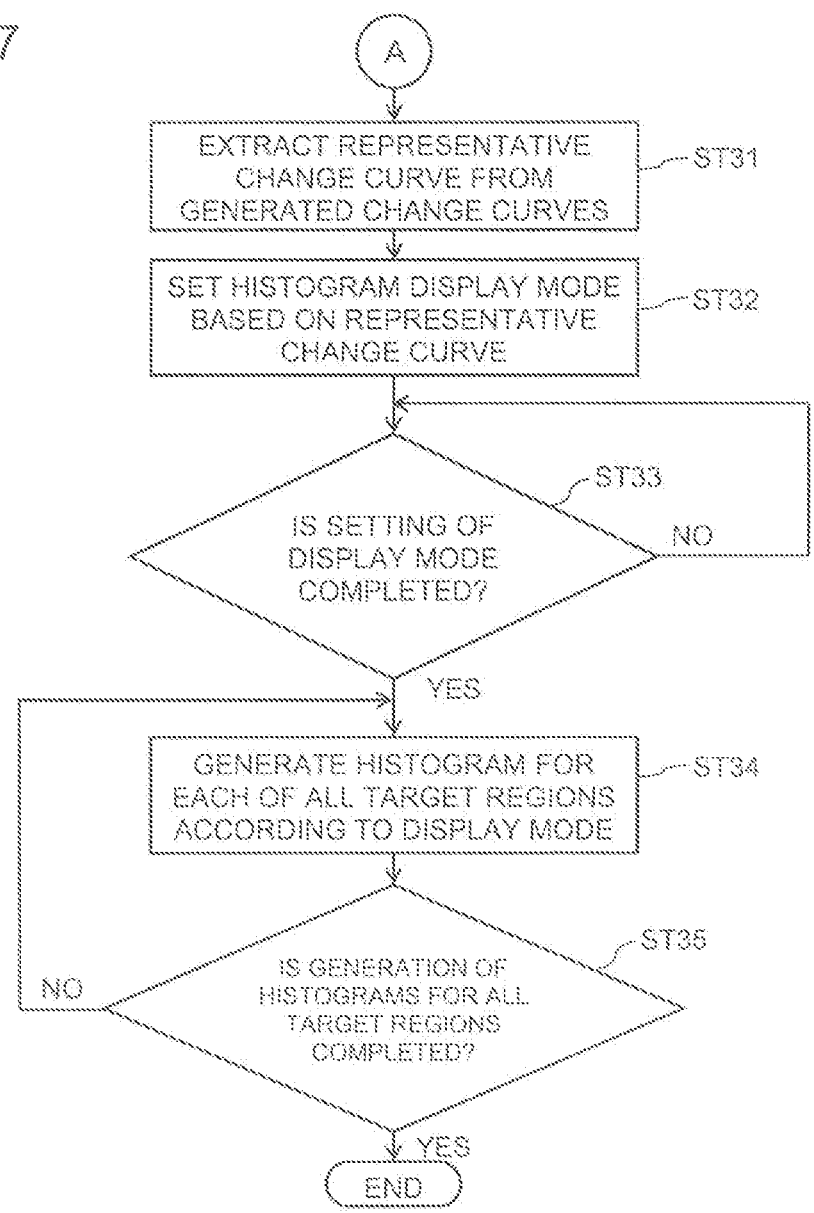
FIG. 17 is a detailed flowchart of a histogram generating process in the flowchart of FIG. 14 according to the embodiment.

FIGS. 16 and 17 are detailed flowcharts illustrating the histogram generating process in the flowchart of FIG. 14. The processing circuit 44 generates histograms using the data acquisition function 444 and the display information generating function 445.

First, the processing circuit 44 sets the representative image (step ST21 in FIG. 16). Specifically, the processing circuit 44 sets the position, orientation, or thickness of the selected representative image. The thickness of the representative image is set because the change curve of the pixel value data changes as the thickness of the representative image changes.

Upon completion of the setting of the representative image, the processing circuit 44 starts setting regions for histogram generation (step ST22). The processing circuit 44 sets a grid (step ST23). The roughness of the grid may be changed (step ST24). Having received an input signal from the operator through the input interface 43 to change the roughness of the grid (YES in step ST24), the processing circuit 44 changes it.

When the roughness of the grid is not changed (NO in step ST24) or upon completion of changing the roughness of the grid, as described with reference to FIG. 2, the processing circuit 44 sets a target region (a region for which a histogram is to be generated) using, for example, the grid or ROI in an arbitrary shape (step ST25). The processing circuit 44 may set a region (excluded region) where no histogram is to be generated (step ST26).

Then, the processing circuit 44 determines whether the setting of target regions is completed (step ST27). If the setting is not completed (NO in step ST27), the process returns to the step ST22 to further set a target region. On the other hand, when the setting of target regions is completed (YES in step ST27), the processing circuit 44 generates the change curve of the CT values (pixel value data) of all the time phases indicated by the selected medical image data with respect to each of the target regions (step ST28).

Thereafter, the processing circuit 44 adjusts the positions of generated change curves based on a reference time phase (step ST29). Although the change curve of the pixel value data has been described as being generated by the processing circuit 44 with the data acquisition function 444, it may not necessarily be generated as explained in connection with FIGS. 3 and 4.

The processing circuit 44 checks whether the change curve of the pixel value data has been generated for all the target regions in the medical images of a purity of time phases acquired (step ST30).

When the change curve has not been generated for all the target regions (NO in step ST30), the process returns to step ST28 to further generate the change curve for a remaining region. On the other hand, when the change curve has been generated for all the target regions (YES in step ST30), a representative change curve is extracted from the change curves (step ST31 in FIG. 17) to set the histogram display mode (step ST32).

The histogram display mode is set as described with reference to FIG. 5. The processing circuit 44 checks whether the setting of the display mode has been completed (step ST33). When the setting has not been completed (NO in step ST33), the processing circuit 44 is on standby.

When the setting of the display mode is completed (YES in step ST33), the processing circuit 44 generates a histogram for each of all the target regions using the display information generating function 445 according to the display mode thus set (step ST34).

The processing circuit 44 checks whether a histogram has been generated for all the target regions (step ST35). If the generation of histograms has not been completed (NO in step ST35), the process returns to step ST34 to continue the histogram generating process. On the other hand, when a histogram is generated for each of all the target regions (YES in step ST35), the histogram generating process ends.

As all histograms have been generated, the processing circuit 44 combines the histogram with the representative image using the display control function 446, and displays the composite image of them on the display 42 (step ST7 in FIG. 14).

Note that the processing circuit 44 appropriately changes the display as described above with reference to FIGS. 7 to 13 using the display control function 446 according to an instruction from the operator.

When another composite image of histograms and a representative image is to be displayed (YES in step ST8), the process returns to step ST5, and the processing circuit 44 performs the histogram generating process again after the selection of a representative image. On the other hand, when the display is not particularly changed (NO in step ST8), the process ends.

As described above, according to the embodiment, display information is generated based on medical image data of a plurality of time phases with respect to the same site to be diagnosed, and displayed on an arbitrary cross section. With this, changes in the medical image data can be quantitatively presented with the accurate position of the subject by a simple operation. Thus, it is possible to reduce the time from image processing to the diagnosis, thereby improving the working efficiency.

Second Embodiment

Next, a second embodiment will be described. In the second embodiment, like constituent elements as those described in the first embodiment are designated by like reference numerals, and the same description is not repeated.

While the first embodiment describes an example in which histograms are generated with the medical image diagnosis apparatus 1, the second embodiment describes an example in which histograms are generated with a medical image processing apparatus 50.

[Configuration of Medical Image Processing Apparatus]

Figure 18:
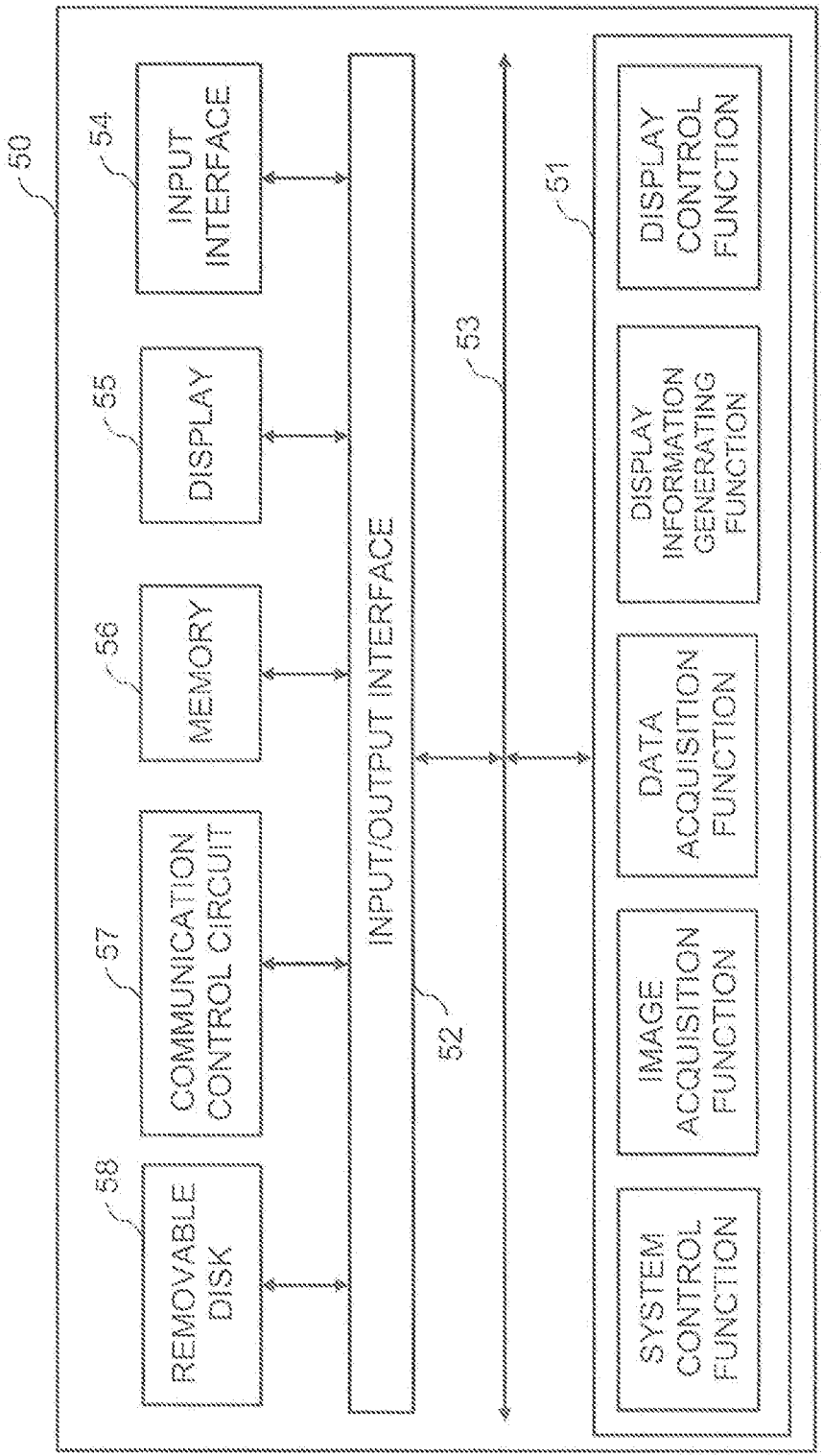
FIG. 18 is a block diagram illustrating the overall configuration of a medical image processing apparatus according to a second embodiment.

FIG. 18 is a block diagram illustrating the overall configuration of the medical image processing apparatus 50 according to the second embodiment.

Examples of the medical image processing apparatus 50 of the embodiment include a medical workstation and a personal computer used by a doctor. The medical image processing apparatus 50 may also be a portable information terminal such as, for example, a portable tablet or a smartphone.

Although the medical image processing apparatus 50 is described as having the configuration illustrated in FIG. 18 in this embodiment, this is by way of example only, and the medical image processing apparatus 50 may have any configuration. In other words, the medical image processing apparatus 50 may have a configuration other than that illustrated in FIG. 18. Further, the medical image processing apparatus 50 may be a single apparatus or a set of apparatuses fixed in a room, or may be portable.

Further, the medical image processing apparatus 50 may be configured as an independent apparatus, or may be configured to form all or part of various management systems built in a medical institution such as a hospital information system (HIS), a radiological information system (RIS), and a picture archiving communication system (PACS).

The medical image processing apparatus 50 includes a processing circuit 51 and an input/output interface 52, which are connected via a bus 53. The medical image processing apparatus 50 further includes an input interface 54, a display 55, a memory 56, a communication control circuit 57, and a removable disk 58, which are connected to the input/output interface 52.

The processing circuit 51 controls each part of the medical image processing apparatus 50. Specifically, the processing circuit 51 includes, for example, a central processing unit (CPU), a read only memory (ROM), and a random access memory (RAM) (not illustrated).

The CPU reads out a boot program for activating the medical image processing apparatus 50 from the ROM based on an input signal from the input interface 54 and executes it. The CPU also reads out various operating systems stored in the memory 56. The processing circuit 51 also controls various apparatuses based on input signals received from external devices (not illustrated) through the input interface 54 or the input/output interface 52.

In addition, the CPU loads programs and data from the RAM, the memory 56, or the like to the RAM. Then, the CPU generates histograms using medical image data of a plurality of time phases based on, for example, commands of a program read out from the RAM, and controls the display 55 to display them. The CPU also implements a series of processes such as data computation and processing. Details of the processing circuit 51 will be described later.

The input interface 54 receives various input operations from the operator of the medical image processing apparatus 50. The input interface 54 generates an input signal based on the operation of the operator, and sends the input signal to the processing circuit 51 via the bus 53. As the input interface 54, for example, GUI or input devices such as buttons, a keyboard, a trackball, a touch panel displayed on the display 55, and the like may be used.

The display 55 may be, for example, a liquid crystal display (LCD) or an organic EL (Electroluminescence) display. The display 55 receives an output signal from the processing circuit 51 via the bus 53, and displays, for example, a composite image of the histograms generated and a representative image, a processing result of the processing circuit 51, an operation screen (for example, GUI for receiving various instructions from the operator), and the like.

The memory 56 is formed of, for example, a semiconductor, a magnetic disk, or the like. The memory 56 stores data and programs to be executed by the processing circuit 51. For example, the memory 56 stores a program for generating histograms. When the processing circuit 51 implements the program, the medical image processing apparatus 50 is enabled to perform the processes described in the first embodiment such as the acquisition of medical image data of a plurality of time phases, the acquisition of pixel value data of a plurality of time phases using the medical image data, and the generation of display information (histogram) based on the pixel value data.

The communication control circuit 57 may be, for example, a local area network (LAN) card, a modem, or the like, and enables the medical image processing apparatus 50 to connect to a communication network such as the Internet or LAN. Data received from the communication network through the communication control circuit 57 is sent as an input signal to the processing circuit 51 via the input/output interface 52 and the bus 53. Data output from the processing circuit 51 via the input/output interface 52 and the bus 53 is transmitted as an output signal to the communication network through the communication control circuit 57.

For example, the communication network connects the medical image processing apparatus 50 and an image storage server or the like, and enables the exchange of, for example, medical image data between them. Examples of the communication network include the Internet, LAN, and the like. Information exchanged via the communication network may be in conformity with any standard such as digital imaging and communication in medicine (DICOM) or the like. The connection to the communication network or the like may be either wired or wireless.

The removable disk 58 is an optical disk or a flexible disk, and signals read and written by the disk drive are transmitted to and received from the processing circuit 51 via the input/output interface 52 and the bus 53. The removable disk 58 may store, for example, the program for generating histograms. In this case, the program is loaded from the removable disk 58 and implemented in the medical image processing apparatus 50. The removable disk 58 may not be included in the medical image processing apparatus 50.

The processing circuit 51 implements a system control function, an image acquisition function, a data acquisition function, a display information generating function, and a display control function. In the claims, the image acquisition unit corresponds to the image acquisition function, the data acquisition unit corresponds to the data acquisition function, the generation unit corresponds to the display information generating function, and the display control unit corresponds to the display control function.

The system control function, the image acquisition function, the data acquisition function, the display information generating function, and the display control function of the processing circuit 51 are performed in the same manner as described in the first embodiment. Therefore, the description of them will not be repeated.

The system control function, the image acquisition function, the data acquisition function, the display information generating function, and the display control function of the processing circuit 51 can be realized by a software program that is executed by a processor (the processing circuit 51) and stored in a predetermined memory (the memory 56), the removable disk 58, or the like. The term "processor" as used herein refers to a circuit such as, for example, a dedicated or general central processing unit (CPU) arithmetic circuit (circuitry), an application specific integrated circuit (ASIC), a programmable logic device such as a simple programmable logic device (SPLD) and a complex programmable logic device (CPLD), a field programmable gate array (FPGA), or the like.

The processor reads out, for example, a program stored in the memory 56 or directly incorporated in the circuit of the processor and executes it, thereby realizing the functions. Each processor may be provided with the memory 56 for storing the program. The memory 56 may store, for example, a program corresponding to the system control function, the image acquisition function, the data acquisition function, the display information generating function, and the display control function of the processing circuit 51 illustrated in FIG. 18. The memory 56 has a structure as described above.

As described above, according to the embodiment, display information is generated based on medical image data of a plurality of time phases with respect to the same site to be diagnosed, and displayed on an arbitrary cross section. With this, changes in the medical image data can be quantitatively presented with the accurate position of the subject by a simple operation. Thus, it is possible to reduce the time from image processing to the diagnosis, thereby improving the working efficiency.

While certain embodiments have been described, these embodiments have been presented by way of example only, and are not intended to limit the scope of the inventions. Indeed, the novel embodiments described herein may be embodied in a variety of other forms; further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus, comprising processing circuitry configured to:
    acquire medical image data of a plurality of time phases;
    acquire pixel value data of the plurality of time phases with respect to a specified region based on the medical image data of the plurality of time phases;
    generate display information based on the pixel value data of the plurality of time phases, the display information being a column representing change of a pixel value over time; and
    display a composite image in which the display information is arranged on the specified region on medical image data of an arbitrary time phase that is selected from the medical image data of the plurality of time phases.

2. The medical image diagnosis apparatus of claim 1, wherein the processing circuitry is further configured to divide the pixel value data of the time phases into a plurality of ranges such that the display information is displayed in different display modes depending on the ranges.

3. The medical image diagnosis apparatus of claim 1, wherein the processing circuitry is further configured to display the display information according to a display range set.

4. The medical image diagnosis apparatus of claim 2, wherein the processing circuitry is further configured to display the display information according to a display range set.

5. The medical image diagnosis apparatus of claim 1, wherein the processing circuitry is further configured to process the display information according to conditions set by an operator before displaying the display information.

6. The medical image diagnosis apparatus of claim 2, wherein the processing circuitry is further configured to process the display information according to conditions set by an operator before displaying the display information.

7. The medical image diagnosis apparatus of claim 3, wherein the processing circuitry is further configured to process the display information according to conditions set by an operator before displaying the display information.

8. The medical image diagnosis apparatus of claim 1, wherein the processing circuitry is further configured to generate the display information each time the pixel value data of the plurality of time phases is acquired.

9. The medical image diagnosis apparatus of claim 2, wherein the processing circuitry is further configured to generate the display information each time the pixel value data of the plurality of time phases is acquired.

10. The medical image diagnosis apparatus of claim 3, wherein the processing circuitry is further configured to generate the display information each time the pixel value data of the plurality of time phases is acquired.

11. The medical image diagnosis apparatus of claim 5, wherein the processing circuitry is further configured to generate the display information each time the pixel value data of the plurality of time phases is acquired.

12. A medical image processing apparatus, comprising processing circuitry configured to:
    acquire medical image data of a plurality of time phases;
    acquire pixel value data of the plurality of time phases with respect to a specified region based on the medical image data of the plurality of time phases;
    generate display information based on the pixel value data of the plurality of time phases, the display information being a column representing change of a pixel value over time; and
    display a composite image in which the display information is arranged on the specified region on medical image data of an arbitrary time phase that is selected from the medical image data of the plurality of time phases.

* * * * *